(12) United States Patent
Anderson, Jr. et al.

(10) Patent No.: US 9,521,062 B2
(45) Date of Patent: Dec. 13, 2016

(54) COMMUNICATION TEST FRAMEWORK

(75) Inventors: Don R. Anderson, Jr., Indianapolis, IN (US); David B. Markisohn, Indianapolis, IN (US); Robert E. Reinke, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 751 days.

(21) Appl. No.: 13/242,546

(22) Filed: Sep. 23, 2011

(65) Prior Publication Data

US 2013/0080570 A1    Mar. 28, 2013

(51) Int. Cl.
*G06F 15/16* (2006.01)
*H04L 12/26* (2006.01)
*G06F 11/27* (2006.01)
*G06F 11/263* (2006.01)
*G06F 19/00* (2011.01)

(52) U.S. Cl.
CPC ........... *H04L 43/50* (2013.01); *G06F 19/3418* (2013.01)

(58) Field of Classification Search
CPC ........ H04L 43/00; H04L 43/065; H04L 43/50; H04L 43/18; H04L 69/02; H04L 29/12009; H04L 29/12358; H04L 29/125; H04L 47/193; H04L 47/29; H04L 47/30; H04L 47/36; H04L 47/365; H04L 61/251; H04L 61/2564; H04L 69/16; H04L 69/167; H04L 69/03; H04L 29/06; H04L 29/06027; H04L 69/08; H04L 69/18; G06F 11/30; G06F 11/34; G06F 17/28; G06F 17/289; G06F 17/212; G06F 17/2735; G06F 17/30345; G06F 17/30563; G06F 21/44; G06F 3/067; G06F 9/30145; G06F 9/54; G06F 11/2069; G06F 11/3688; G06F 12/0246; G06F 12/0831; G06F 12/0862; G06F 12/1027; G06F 13/4286; G06F 15/78; G06F 17/275; G06F 17/2836; G06F 17/2854; G06F 17/30011; G06F 17/30194; G06F 17/30389; G06F 17/30867; G06F 17/30873; G06F 19/321; G06F 19/325; G06F 11/2294; G06F 11/27; G06F 11/263; G06F 11/2733; G06F 11/362; G06F 11/3684
USPC ........ 709/203, 223–227, 217–219, 201, 202; 715/764, 771; 703/13, 27; 379/10.01, 379/1.01; 370/241, 466, 469, 395.5
See application file for complete search history.

(56) References Cited

U.S. PATENT DOCUMENTS

| | | | |
|---|---|---|---|
| 5,612,898 A | 3/1997 | Huckins | |
| 6,393,437 B1 * | 5/2002 | Zinda et al. | 717/124 |
| 7,155,639 B2 | 12/2006 | Gorshenev et al. | |
| 7,286,953 B1 * | 10/2007 | Li et al. | 702/123 |
| 7,467,078 B2 * | 12/2008 | Smith | 703/25 |

(Continued)

*Primary Examiner* — Anthony Mejia
*Assistant Examiner* — Linh T Nguyen
(74) *Attorney, Agent, or Firm* — Harness Dickey

(57) ABSTRACT

A protocol-independent tool for debugging and testing communication interfaces of devices and systems is disclosed. The tool is configured to receive protocol plug-ins corresponding to different communication protocols. Given a plug-in, the tool instantiates the plug-in's implementation of tool-defined stack interface. Through this interface and its implementation by the plug-in, the tool can communicate with a device being tested. The protocol plug-in receives commands from a command interface for the device being tested, generates data packets in accordance with the communication protocol implemented by the plug-in, and transmits the data packets to the device being tested.

20 Claims, 13 Drawing Sheets

(56) References Cited

U.S. PATENT DOCUMENTS

| | | | |
|---|---|---|---|
| 7,496,815 B2* | 2/2009 | Bhaumik | H04L 12/2697 |
| | | | 714/25 |
| 7,623,856 B2 | 11/2009 | Azuma | |
| 7,805,533 B2* | 9/2010 | Burns et al. | 709/230 |
| 7,813,292 B2 | 10/2010 | Reinhold | |
| 7,836,164 B2* | 11/2010 | Tawfik | 709/223 |
| 8,019,796 B1* | 9/2011 | Chand et al. | 707/803 |
| 8,195,419 B2* | 6/2012 | Conner | G01R 31/31919 |
| | | | 398/45 |
| 8,788,685 B1* | 7/2014 | Boyles | G06F 11/3688 |
| | | | 709/217 |
| 2001/0011215 A1* | 8/2001 | Beeker | H04L 41/145 |
| | | | 703/27 |
| 2003/0139944 A1* | 7/2003 | Carlsen | G06F 19/322 |
| | | | 705/2 |
| 2003/0231741 A1* | 12/2003 | Rancu | H04M 3/303 |
| | | | 379/9 |
| 2006/0094413 A1* | 5/2006 | Evans et al. | 455/418 |
| 2008/0010553 A1* | 1/2008 | Betawar | G06F 11/263 |
| | | | 714/46 |
| 2008/0208374 A1* | 8/2008 | Grgic et al. | 700/83 |
| 2009/0113245 A1* | 4/2009 | Conner | 714/33 |
| 2009/0150549 A1* | 6/2009 | Young et al. | 709/227 |
| 2010/0011352 A1* | 1/2010 | Chu et al. | 717/174 |
| 2010/0042874 A1* | 2/2010 | Lee | 714/27 |
| 2011/0004460 A1* | 1/2011 | Duffie et al. | 703/28 |
| 2011/0051174 A1* | 3/2011 | Hattori | 358/1.15 |

\* cited by examiner

COMMUNICATION TEST FRAMEWORK

FIELD

The present disclosure relates to a protocol independent debugging tool.

BACKGROUND

Increasingly, the health care industry is turning to electronic medical devices to assist in the treatment of medical conditions. These electronic medical devices will often be part of a system of devices that are configured to communicate with one another and to other systems such as mobile phones over a variety of communication protocols. Further, many of these devices communicate data that is used to provide treatment to the patient. For instance, a blood glucose meter may communicate an amount of bolus to deliver to an insulin pump. As can be appreciated, the sensitivity of such communications cannot be overstated. Thus, developers must take extra care to ensure that these devices are able to properly communicate in a wide variety of conditions.

Testing the communications interfaces on medical and non-medical devices has traditionally required that a developing entity build or buy a debugging tool for each communications interface on the device. These debugging tools are configured to communicate with the device being tested using the communication protocol(s) of the device. This approach, however, is inefficient as for every new product using a new protocol, the developing entity must construct or purchase a new tool to debug and test the communication interfaces of the new product. Further, as new communication protocols are developed, developers must develop new debugging tools to support the new communication protocols. Thus, there is a need to provide a generic, extensible framework for communication interface debug/test tools. Further, there is a need for an extensible user interface that provides for the ability to update command definitions used to debug devices being tested.

The background description provided herein is for the purpose of generally presenting the context of the disclosure.

SUMMARY

In an aspect of the disclosure, a tool for testing a plurality of different devices having different device types is disclosed. The plurality of different device types have different communication protocols associated therewith. The tool comprises a plurality of communication modules, each communication module having a different physical transport for communicating with one or more of the plurality of different device types. Each communication module is configured to communicate using at least one of the plurality of different communication protocols. The tool further comprises a protocol manager that determines a plurality of available protocol plug-ins, and that receives a protocol selection corresponding to one of the available protocol plug-ins. Each protocol plug-in of the plurality of available protocol plug-ins supports one of the different communication protocols. The tool further includes a stack broker that instantiates a protocol plug-in from the plurality of available protocol plug-ins, the protocol plug-in corresponding to the protocol selection. Each protocol plug-in from the plurality of available protocol plug-ins implements a common stack interface and is configured to: a) when commanded over the common stack interface, open a communication session with a device being tested over one of the plurality of communication modules, and b) when commanded over the common stack interface, generate one or more data packets intended for the device being tested according to the communication protocol supported by the protocol plug-in. The protocol manager is further configured to receive a command for the test device and to receive at least one parameter value corresponding to the command, and to provide the instantiated protocol plug-in with the command and the at least one parameter value. The instantiated protocol plug-in: i) receives the command and the at least one parameter value, ii) generates one or more packets for the device being tested according to the communication protocol corresponding to the instantiated protocol plug-in, and iii) communicates the one or more packets to the device being tested using the open communication session.

In another aspect of the disclosure, a method for configuring a tool for testing a plurality of different devices having different device types. The plurality of different devices each have a different communication protocol associated therewith. The tool includes a plurality of communication modules, each communication module having a different physical transport for communicating with one or more of the plurality of different device types. Each communication module is configured to communicate using at least one of the plurality of different communication protocols. The method comprises determining a plurality of available protocol plug-ins, each protocol plug-in of the plurality of available protocol plug-ins supporting one of the different communication protocols. The method further comprises receiving a protocol selection corresponding to one of the available protocol plug-ins. Each protocol plug-in implements a common stack interface. The method further includes instantiating a protocol plug-in corresponding to the protocol selection, and receiving a command for a test device and at least one parameter value corresponding to the command. The method further comprises providing the instantiated protocol plug-in with the command and the at least one parameter value. The instantiated protocol plug-in is configured to perform: i) opening a communication session with a device being tested over one of the plurality of communication modules, ii) receiving the command and the at least one parameter value, iii) generating one or more data packets for the device being tested according to the communication protocol corresponding to the instantiated protocol plug-in, and iv) communicating the one or more packets to the device being tested using the open communication session.

Further areas of applicability of the present disclosure will become apparent from the detailed description provided hereinafter. It should be understood that the detailed description and specific examples are intended for purposes of illustration only and are not intended to limit the scope of the disclosure.

Figure 1:
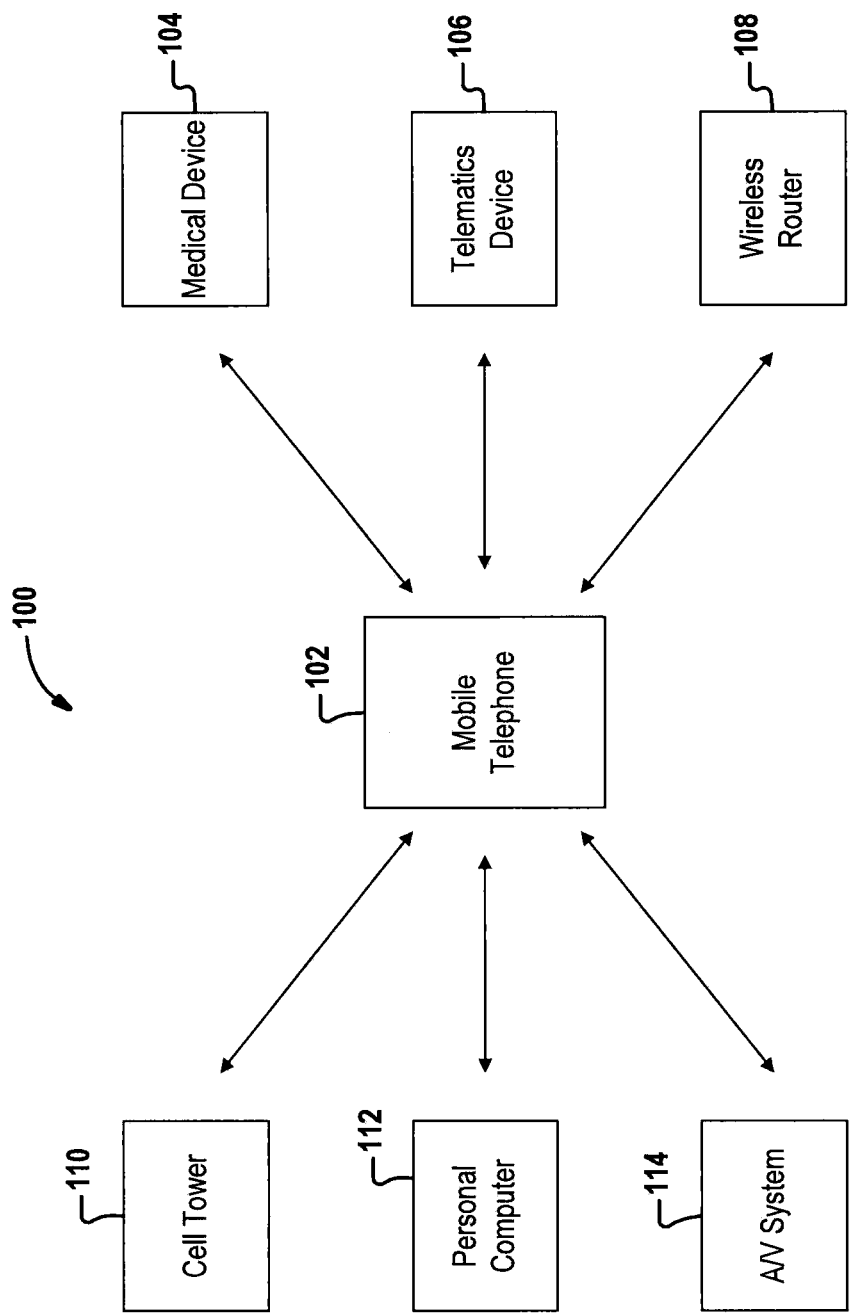
FIG. 1 is a block diagram illustrating an exemplary system of devices communicating with a mobile telephone.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Increasingly, consumer electronics, including medical devices, are becoming more complex. So too are the communication capabilities of the devices. These devices are configured to communicate with a plurality of different device types using a wide umbrella of communication protocols. FIG. 1 illustrates an exemplary system 100, e.g., mobile telephone 102 and a set of devices 104-112 that the mobile telephone 102 communicates with. For instance, the mobile telephone 102 can be configured to communicate with a personal computer 112 over a USB connection and utilizing the USB protocol. The mobile telephone 102 can be configured to communicate with a telematics device 106 of a vehicle over a wireless Bluetooth® connection utilizing the Bluetooth® protocol. The mobile telephone 102 may also be configured to communicate wirelessly with a wireless router 108 using IEEE 802.11 protocol and with a cell tower utilizing a CDMA or GSM protocol. It is appreciated that the mobile telephone 102 may be configured to communicate with a plurality of different devices not shown over a plurality of different communication protocols not listed or not yet developed. Further, the example of FIG. 1 is provided for example only and it is appreciated that the exemplary system 100 can be any device configured to communicate with another device or component of a device.

Figure 2:
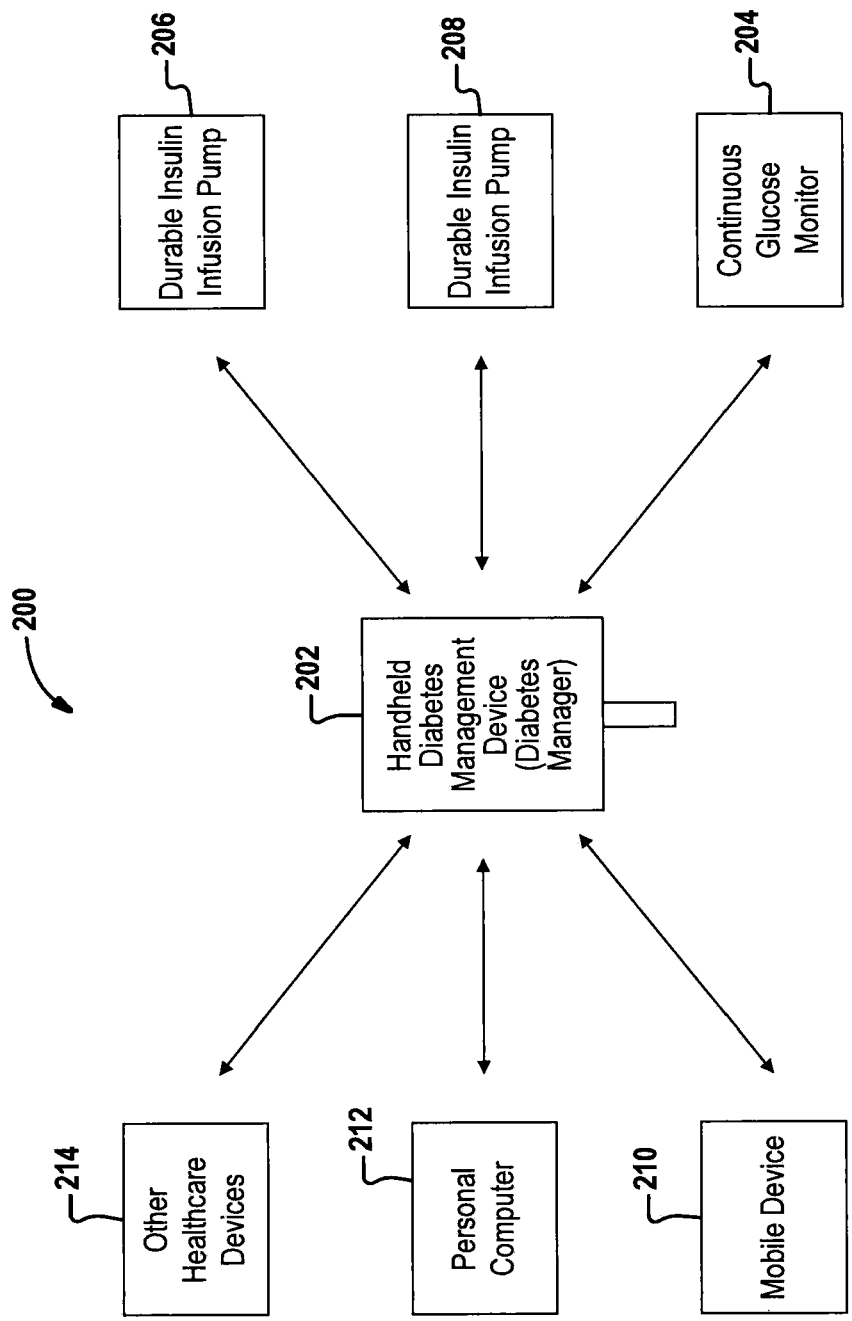
FIG. 2 is a block diagram illustrating an exemplary system of medical devices communicating with a handheld diabetes management device.

Medical devices are also becoming increasingly connected. Referring to FIG. 2, a diabetes management system 200 used by a patient and a clinician includes one or more of the following devices: a diabetes manager 202, a continuous glucose monitor (CGM) 204, an insulin pump 206 or 208, a mobile device 210, a PC 212 with the diabetes analysis software, and other healthcare devices 214. The diabetes manager 202 is configured as a system hub and communicates with the devices of the diabetes management system 200. Alternatively, the insulin pump 206 or the mobile device 210 can serve as the system hub. Communication between the devices in the diabetes management system 200 can be performed using wireless interfaces (e.g., Bluetooth®) and/or wired interfaces (e.g., USB). Communication protocols used by these devices can include protocols compliant with the IEEE 11073 standard as extended using guidelines provided by Continua® Health Alliance Design Guidelines.

The diabetes manager 202 can receive glucose readings from one or more sources (e.g., from the CGM 204). The CGM 204 continuously measures the interstitial glucose level of the patient. The CGM 204 periodically communicates the glucose level to the diabetes manager 202. The diabetes manager 202 and the CGM 204 can be configured to communicate wirelessly using a proprietary wireless protocol (e.g., Gazell wireless protocol developed by Nordic Semiconductor, Inc.).

Additionally, the diabetes manager 202 includes a blood glucose meter (BGM) and a port that communicates with the BGM (not shown). The port can receive a blood glucose measurement strip. The patient deposits a sample of blood or other bodily fluid on the blood glucose measurement strip. The BGM analyzes the sample and measures the blood glucose level in the sample. The blood glucose level measured from the sample and/or the glucose level read by the CGM 204 can be used to determine the amount of insulin to be administered to the patient. To facilitate collection of blood glucose measures, the diabetes manager 202 may execute one or more structured collection procedures, which may require communication between different devices.

The diabetes manager 202 communicates with the insulin pump 206 or 208 utilizing one or more communication protocols, e.g., protocols corresponding to radio/frequency, infrared, or wired communications. The insulin pump 206 or 208 can be configured to receive instructions from the diabetes manager 202 to deliver a predetermined amount of insulin to the patient. Additionally, the diabetes manager 202 can receive other information from the patient including meal and/or exercise schedules of the patient. The diabetes manager 202 can determine the amount of insulin to administer based on the additional information.

The insulin pump 206 or 208 can also communicate data to the diabetes manager 202. The data can include amounts of insulin delivered to the patient, corresponding times of delivery, and pump status. The diabetes manager 202 and the insulin pump 206 or 208 can communicate using a wireless communication protocol such as Bluetooth®. Other wireless or wired communication protocols can also be used.

In addition, the diabetes manager 202 can communicate with the other healthcare devices 214. For example, the other healthcare devices 214 can include a blood pressure meter, a weight scale, a pedometer, a fingertip pulse oximeter, a thermometer, etc. The other healthcare devices 214 obtain and communicate personal health information of the patient to the diabetes manager 202 through wireless, USB, or other interfaces. The other healthcare devices 214 may use communication protocols compliant with ISO/IEEE 11073. The diabetes manager 202 can communicate with the other healthcare devices 214 using interfaces including Bluetooth®, USB, etc. Further, the devices of the diabetes management system 200 can communicate with each other via the diabetes manager 202. The diabetes manager 202 can communicate with the PC 212 using USB, or other wired or wireless interfaces, such as Bluetooth®.

The diabetes manager 202 can communicate with the mobile device 210 using Bluetooth®. The mobile device 210 may include a cellular phone, a pager, or a tablet. The diabetes manager 202 can send data to an external network through the mobile device 210. The mobile device 210 can transmit messages to the external network upon receiving data from the diabetes manager 202.

It is noted that the example of FIGS. 1 and 2 is provided for example only and the types of devices are not intended to limit the scope of the disclosure.

As can be appreciated from the foregoing examples of FIG. 1 and FIG. 2, a single device may be configured to communicate over a wide variety of communication mediums utilizing a plurality of different communication protocols. Further, to enable communication between some devices, more than one communication protocol may be required. For instance, in the example of medical devices that communicate with one another, the devices may be required to communicate utilizing communication protocol IEEE 11073 in addition to the communication protocol that is used to communicate over the communication interface of the devices, e.g., USB, Bluetooth®, and IEEE 802.11. As a result, a communicating device must be configured to send and receive data packets according to one or more communication protocols. Furthermore, even known communication protocols are subject to changes and updates.

Figure 3:
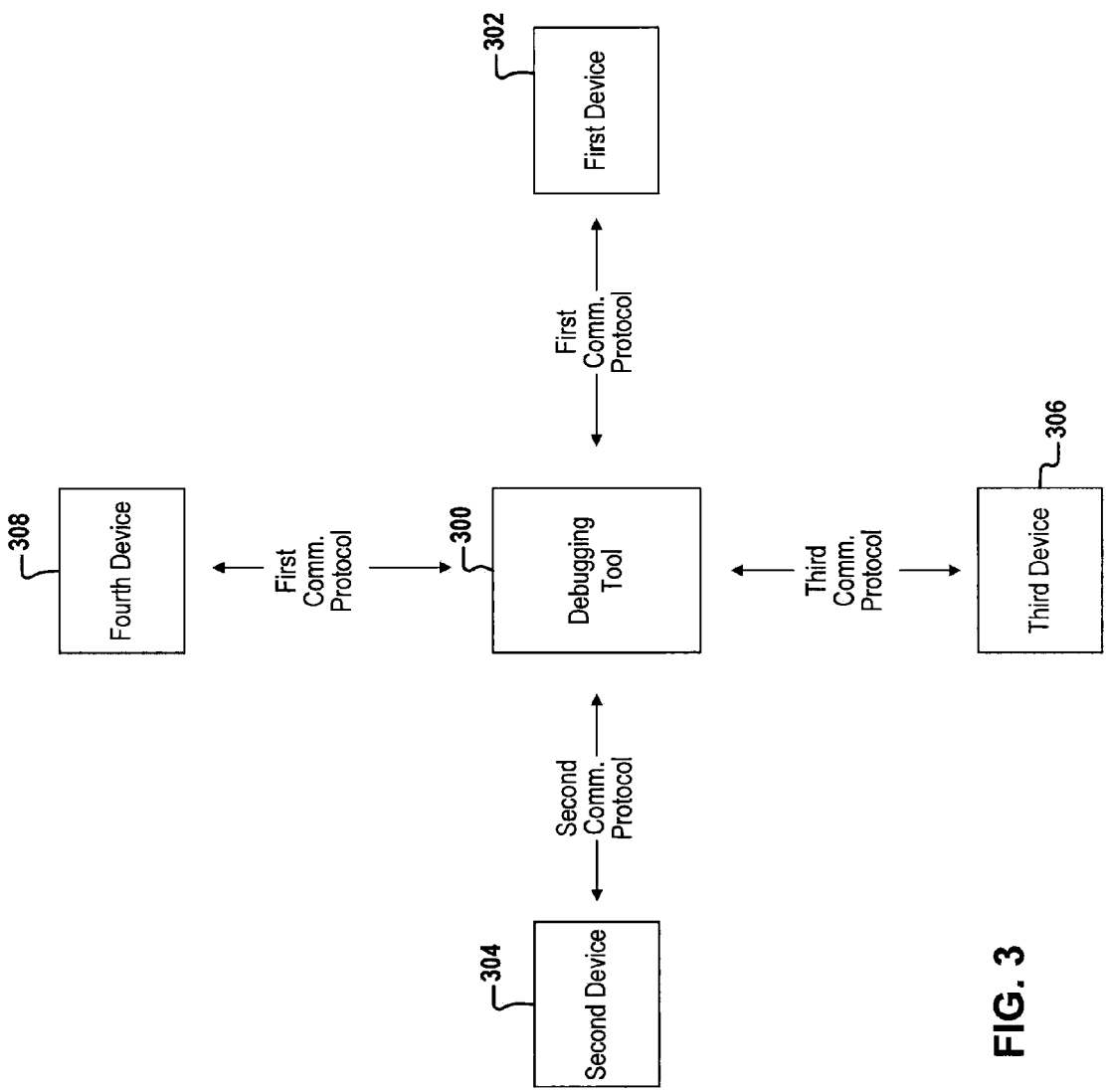
FIG. 3 is a block diagram illustrating a protocol independent debugging tool that can test a plurality of different devices over a plurality of different communication protocols.

FIG. 3 illustrates an exemplary debugging tool 300 for debugging different devices 302, 304, 306, and 308 utilizing different communication protocols. The debugging tool 300 is protocol independent, such that it can debug devices using communications protocols of which the tool has no a priori knowledge. Furthermore, the debugging tool 300 can be configured to allow the user to select specific commands for the device being tested without any a priori knowledge on the part of the tool. The debugging tool 300 can be embodied as computer executable instructions that are executed by a processor of a computing device. The computer executable instructions can be stored in a computer readable memory associated with the computing device. The computing device can be any computing device that has requisite communication modules to communicate with a device. For example, to support the 802.11 wireless protocols, the computing device needs to have a wireless transceiver. It is appreciated that the computing device can be updated with the requisite communication modules as the communication modules are needed. It is understood that a communication module includes a physical transport for interfacing between a device and the computer.

As can be seen from FIG. 3, the debugging tool 300 is configured to communicate with a first device 302 using a first communication protocol, with a second device 304 using a second protocol, with a third device 306 using a third protocol, and with a fourth device 308 using the first protocol. It is appreciated that the term devices further includes software systems executing on a personal computer. As discussed, the debugging tool 300 does not have a priori knowledge of the communication protocols or the command definitions of the devices. Thus, the developers of the device to be tested, e.g. the first device 302, can provide the debugging tool 300 with a plug-in for the device and a command definition file for the device being tested. The debugging tool 300 can then build one or more interfaces for communicating with the device being tested.

Figure 4:
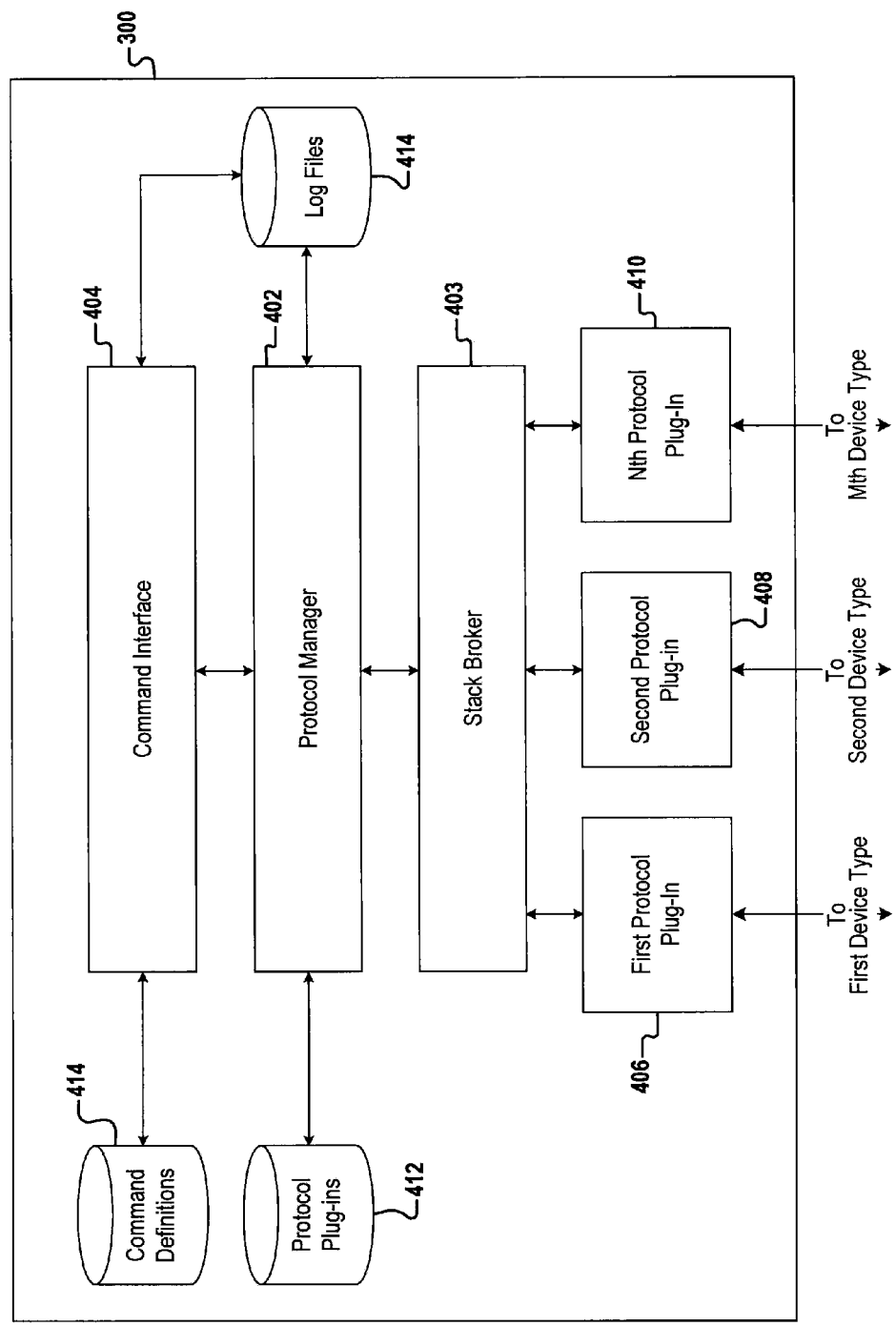
FIG. 4 is a block diagram illustrating exemplary components of a debugging tool.

FIG. 4 illustrates exemplary components of the debugging tool 300. The debugging tool 300 includes a protocol manager 402, a stack broker 403, a command interface 404, a protocol plug-in datastore 412 that stores protocol plug-ins, a command definition file (CDF) datastore 414 that stores command definition files, and a log file datastore 414 that stores results of tests. The stack broker 403 is configured to instantiate one or more protocol plug-ins 406, 408, and 410, to communicate with a first device, a second device, and an Mth device, respectively. It is noted, that some devices may communicate with more than one protocol plug-ins, so it is possible for M to not equal N, but N can equal M.

The protocol manager 402 is configured to determine a set of available protocol plug-ins available to the debugging tool 300. The protocol manager 402 then receives an instruction from the command interface to instantiate one or more protocol plug-ins 406 from the protocol plug-in datastore 412. The protocol manager 402 retrieves and provides the protocol plug-in 406 to the stack broker 403. As will be discussed, the instantiated protocol plug-in 406, at the instruction of the protocol manager 402 via the stack broker 403, opens a communication session with a device being tested over one of the plurality of communication modules of the computing device hosting the debugging tool 300. An instantiated protocol plug-in 406 can generate data packets intended for a device being tested according to a communication protocol supported by the protocol plug-in. The instantiated protocol plug-in 406 can further unwrap data packets from the device being tested and communicate the information received from the device being tested to the protocol manager 402 through the stack broker 403. The protocol manager 402 may be further configured to store the data sent to and received from the device being tested in the log file datastore 416. The protocol manager 402 can also communicate the data communicated from the device being tested to the command interface 404, which in turn can be displayed to the user.

The command interface 404 is configured to allow a user, e.g. a developer or product tester, to communicate commands to the protocol manager 402, and to communicate messages to the user from the protocol manager 402. The command interface 404 can allow a user to enter structured commands or raw commands. Further, the command interface 404 can allow a user to define a sequence of commands or messages to communicate to a device. The command interface 404 retrieves a selected CDF from the CDF datastore 414. A CDF defines the structure of one or more commands or messages for a particular device using a particular protocol. For example, a CDF may define what type of commands a device receives at the application layer and/or the transport layer. Further, a CDF can define parameters of a command, subcommands, and parameters of the subcommands. The command interface 404 utilizes a CDF to provide commands to the protocol manager 402. Furthermore, as will be discussed further below, the command interface 404 provides a user or process with a list of available CDFs in the CDF datastore 414, and receives a CDF selection from the user or process. Based on the CDF selection, the protocol manager 402 retrieves a corresponding protocol plug-in from the protocol plug-in datastore 412, which is provided to the stack broker 403.

A developer can use the debugging tool 300 to test the communication capabilities of the device being tested. The debugging tool 300 is configured such that the architecture of the debugging tool 300 is extensible, such that a developer can develop a new protocol plug-in for a new device/communication protocol, such that the new protocol plug-in is stored in the protocol plug-in datastore 412. When the debugging tool 300 receives a new protocol plug-in, the debugging tool 300 can instantiate the new protocol plug-in, thereby enabling communication with the new device.

In the example of FIG. 4, the stack broker 403 is configured to instantiate a first protocol plug-in 406, a second protocol plug-in 408, and an Nth protocol plug-in 410. While only one protocol plug-in is instantiated at a time, FIG. 4 illustrates that the debugging tool 300 is extensible in that N different protocol plug-ins may be instantiated. It is appreciated that the protocol plug-ins 406, 408, and 410 implement a common stack interface, discussed in greater detail below.

Figure 5:
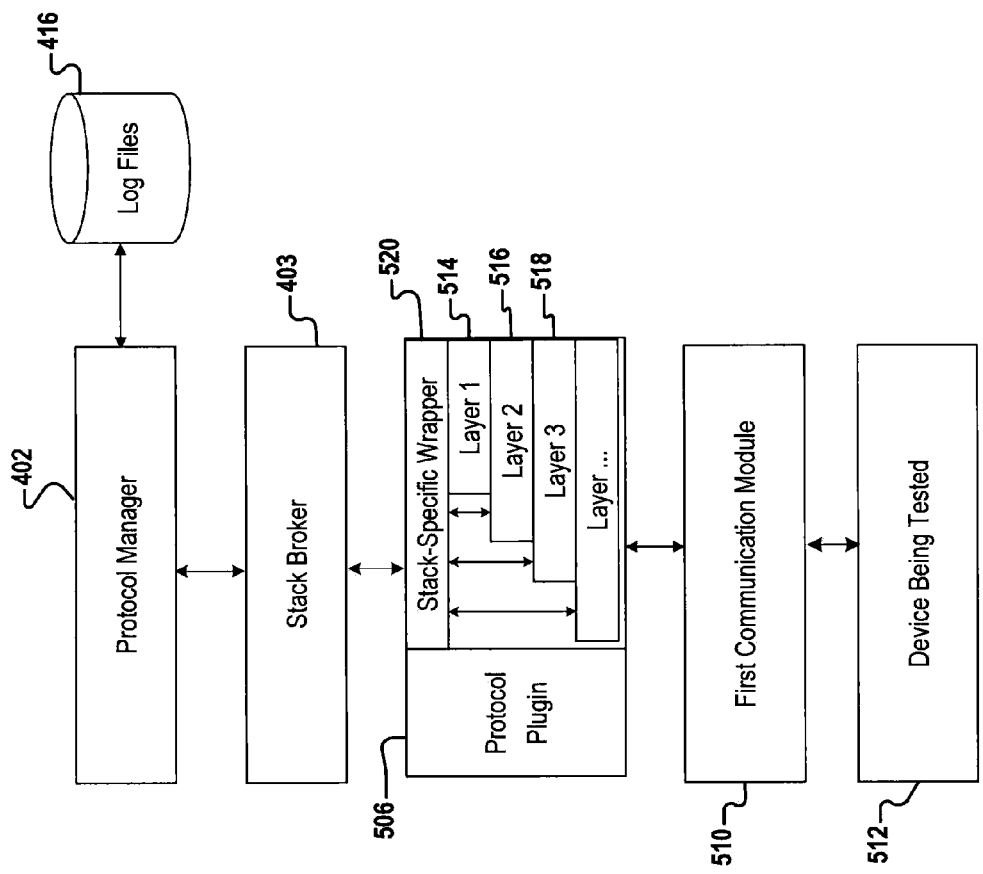
FIG. 5 is a block diagram illustrating exemplary components of a protocol manager of the debugging tool.

FIG. 5 illustrates an exemplary protocol manager 402 in communication with a device being tested 512 via the stack broker 403 and an instantiated protocol plug-in 506. The protocol manager 402 receives commands from the command interface 404 and passes the commands to the stack broker 403. The commands are defined according to a common stack interface, which is described in greater detail below. The stack broker 403 searches the protocol plug-in data store for CDF files, then extracts information about supported protocols from the CDF and presents that information to the caller of the stack broker 403, such as the Command Interface 404. Once a user or process has identified the particular protocol to be used by selecting a CDF, the stack broker 403 locates the protocol plug-in referenced by the selected CDF from the protocol plug-ins datastore 412 and instantiates a stack factory (not shown) from the retrieved protocol plug-in. As will be described below, in some embodiments, the protocol plug-in includes a class with an argument-free constructor implementing the stack factory.

A protocol plug-in, e.g. the first protocol plug-in 506, enables communication between the device being tested 512 and the debugging tool 300. The protocol plug-in 506 receives commands from the command interface 404, via the protocol manager 402, and generates data packets corresponding to the received command in accordance with the communication protocol defined in the protocol plug-in. The commands received by the protocol plug-in 506 are in a format defined by a stack interface that is common across the debugging tool 300, and the protocol plug-in 506, particularly a "stack-specific wrapper" component 520 translates the commands in a format that is compatible with the device being tested 512.

As can be appreciated, a communication protocol includes a plurality of layers. Thus, the protocol plug-in 506 is configured to generate packets by placing parameter values at locations in a data packet corresponding to the different layers of the protocol, e.g., a first layer 514, a second layer 516, and a third layer 518. For example, the first layer 514 may correspond to an application level of the communication protocol, the second layer 516 may correspond to the transport layer of the communication protocol, and the third layer 518 may correspond to the physical layer of the communication protocol. It is appreciated that a communication protocol can have any number of layers, and the foregoing is provided as an example.

A protocol plug-in developer creates the stack-specific wrapper 520 that translates the common language of the debugging tool 300 to the protocol specific language of the device being tested 512. Similarly, the developer prepares the stack-specific wrapper 520 of the protocol plug-in 506 such that the stack-specific wrapper 520 is configured to convert the received data packets in the protocol specific format into the generic format defined by the stack interface. It is appreciated that the developer will also provide a CDF corresponding to the protocol, such that the CDF defines the commands for the device being tested 512, as well as testable parameters for each layer of the communication protocol of the device being tested 512. The CDF defines the commands and the testable parameters in the generic language of the debugging tool 300. As will be described below, the CDF of a particular protocol provides the framework for a user to enter commands to a device that supports that protocol, including testable parameters contained in the commands to the device. The debugging tool 300 can communicate the commands to the stack-specific wrapper 520 of the protocol plug-in 506 corresponding to the device being tested 512 in the generic language, and the stack-specific wrapper 520 of the protocol plug-in 506 generates data packets containing the commands for the device 512 in accordance with the communication protocol of the device and defined in the protocol plug-in 506.

Figure 6A:
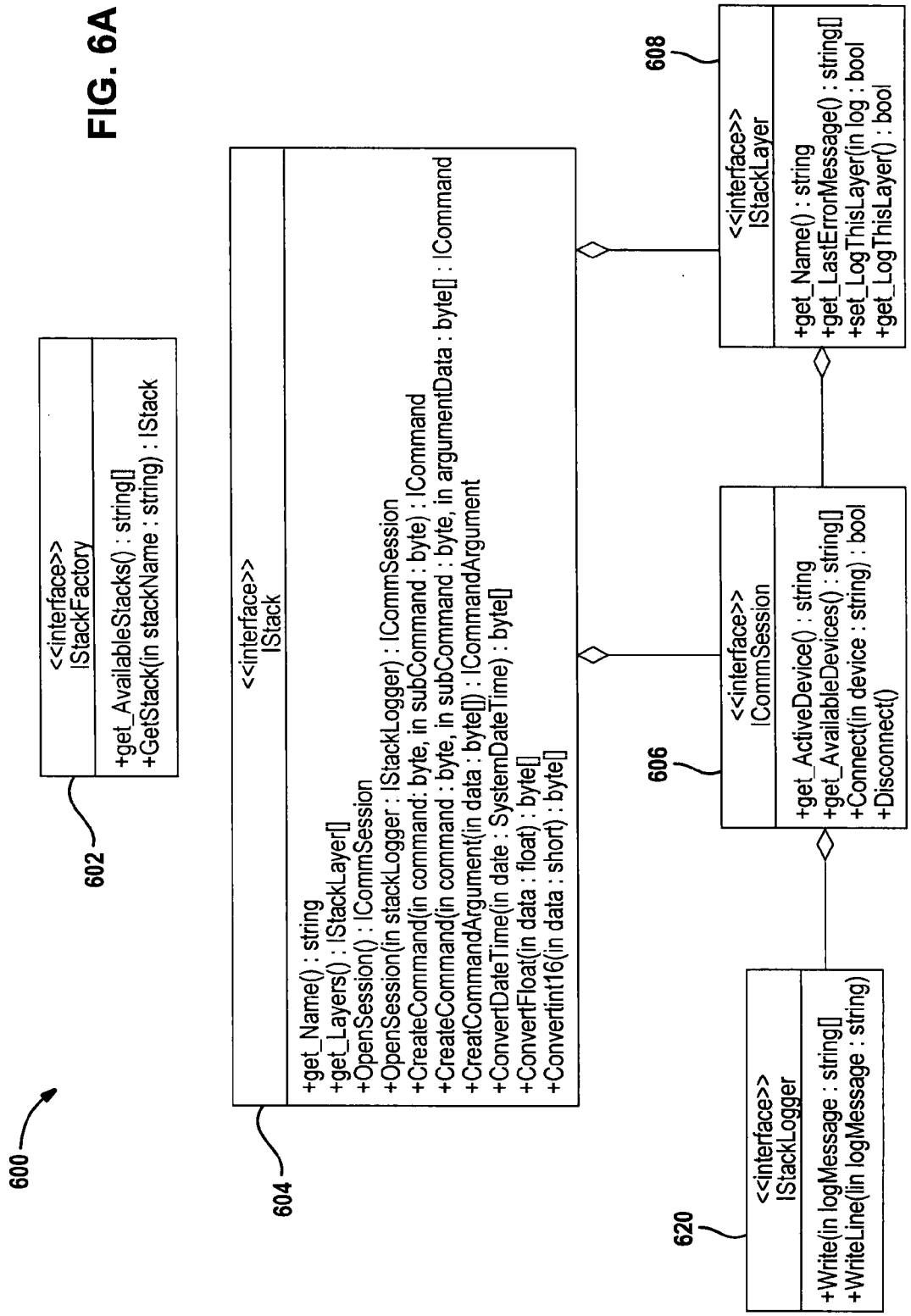
FIGS. 6A and 6B are a class diagram of an exemplary class structure for a protocol plug-in wrapper.
Figure 6B:
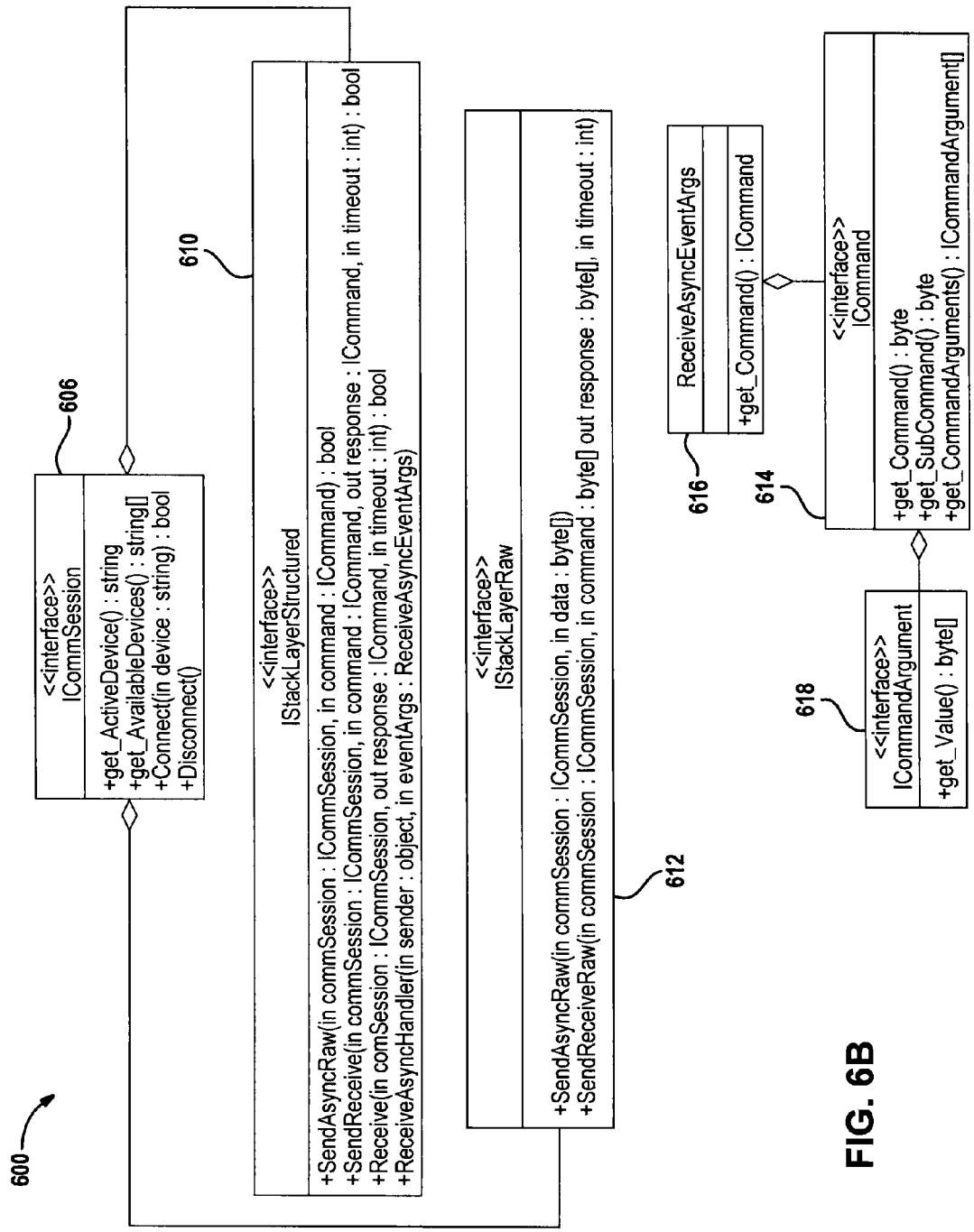

FIGS. 6A and 6B illustrate an exemplary common stack interface definition 600. The exemplary stack interface definition 600 can include an IStackFactory interface 602, an IStack interface 604, an ICommSession interface 606, an IStackLayer interface 608, an IStackLogger interface 620, an IStackLayer structure command interface 610, an IStackLayerRawCommand interface 612, an ICommand interface 614, an ICommandArgument interface 618, and a receive event arguments interface 616. A protocol plug-in implements the stack interface 600, which provides the mechanism by which a protocol plug-in is able to interface with the debugging tool 300.

As was discussed, the protocol manager 402 searches the CDF datastore 414 to find CDFs that refer to protocol plug-ins that implement the stack interface specification 600. The stack interface specification 600 includes specifications for the IStackFactory interface 602. An implementation of the IStackFactory is a top level object in a plug-in that the stack broker 403 uses to communicate with lower level objects in the plug-in. In an exemplary implementation, an IStackFactory instance can be created by the stack broker 403 using reflection. For instance, the stack broker 403 will call an argument free constructor, thereby implementing an instance of the IStackFactory.

The exemplary IStackFactory specification 602 defines a plurality of methods that are implemented by the plug-ins, including a method for obtaining available stacks, e.g., "get_AvailableStacks." The method for obtaining available stacks returns a list of protocol stacks that the protocol plug-in supports to the protocol manager 402. A stack factory object is defined in each protocol plug-in; this object contains a method to obtain an instance of a selected stack, e.g., "GetStack." When the user provides a stack selection, e.g. a stack name or identifier, the Stack Broker 403 calls the GetStack method using the definitions of the stack interface 600. It is noted that while the term user can be understood to be a developer, device tester, or user, the present disclosure contemplates that the various methods can present data to an automated script or code operating the debugging tool 300 as well. The GetStack method instantiates and returns an implementation of the selected protocol stack.

The exemplary IStack interface specification 604 defines a plurality of methods that are implemented in a protocol plug-in, including a method to open a communication session e.g. "OpenSession," and a method to generate a command, e.g., "CreateCommand." A method to open a communication session instantiates and returns one or more objects implementing the ICommSession specification 606, thereby allowing the debugging tool 300 to send and receive data to and from the device being tested 512. It is noted that the definition of the open session method can be overloaded to include a method which receives a log file as input. When the overloaded open session method is called, the communications performed over the session are logged in the input log file. It is noted that the log file can be stored in the log file datastore 416.

An open communication session allows the debugging tool 300 to connect to and communicate with a device via one of the communication modules. It is appreciated that the debugging tool 300 has no a priori knowledge of the devices, and therefore, cannot independently discover a device. Thus, the ICommSession specification 606 defines a method for discovering available devices, e.g., "AvailableDevices," which is implemented by the protocol plug-ins in accordance with the communication protocol of a respective protocol plug-in. The available devices method returns a list of devices that are available to communicate with the debugging tool 300 via the communication session instance and the communication module corresponding to the protocol plug-in.

An object implementing the ICommSession specification 606 also includes a method to connect to a device from the list of available devices, e.g., "Connect." The connect method receives a device identifier as an argument and connects to the device indicated by the device identifier. The ICommSession specification 606 also includes an active device property that represents the device with which communication has been established using the connect method. The ICommSession specification 606 also defines a method to disconnect the device, e.g., "Disconnect." It is appreciated that the connect and disconnect methods can be overloaded, such that additional connect and disconnect methods can receive a byte array as a parameter for delivering data to the device upon connecting or disconnecting.

Once a communication session has been instantiated, the stack broker 403 can send commands to and receive responses from the device being tested 512 using the communication session instance. To send commands and receive data, the stack interface object includes a plurality of methods for creating commands for a device, e.g., "CreateCommand." When a command request is received from a user, the create command method is called. The create command method returns an object that implements the ICommand specification 614. The IStack specification 604 also defines a method for creating command arguments e.g., "CreateCommandArguments." The method for creating command arguments instantiates a command argument object implementing the ICommandArgument specification 618. The ICommandArgument specification 618 provides properties to set the command and subcommand bytes. The command arguments are provided to the command object. In order to send a command to the device being tested 512, the command instance and its associated arguments are provided to an object implementing IStackLayerStructured.

The IStack specification 604 also defines methods for converting parameter values provided by the user into a binary format that is compatible with the stack wrapper. These methods receive parameter values and convert them into a byte representation that is in accordance with the communication protocol of the stack interface. These methods can include a method to convert a floating point decimal to a byte representation compatible with the communication protocol of the instantiated protocol plug-in, a method to convert a date and time into a byte representation compatible with the communication protocol of the instantiated protocol plug-in, and a method to convert an integer into a byte representation compatible with the communication protocol of the instantiated protocol plug-in.

As previously discussed, a stack object instantiates one or more stack layer objects defined in the protocol plug-in. A stack layer object corresponds to a layer of the communication protocol implemented by the protocol plug-in. For example, for a particular stack, there may be a first stack layer object for the application layer, a second stack layer object for the transport layer, etc. The IStackLayer interface 608 defines the mechanism by which data is sent and received on an established communication session. The protocol plug-in for a particular communication protocol enables communication to the different stack layers of the particular communication protocol. During the initialization of the stack layer instance, a logger function of the particular layer can be enabled or disabled by setting a Boolean flag that indicates whether messages sent to and from the particular layer should be logged. A stack layer instance may also have an element that contains one or more error messages.

A stack layer object can implement a structured stack layer object that supports sending and receiving structured commands as defined by the IStackLayerStructured interface 610. A stack layer object can also or alternatively implement a raw stack layer object that supports sending and receiving "raw" (unstructured) sequences of bytes, as defined by the IStackLayerRaw interface 612. The IStackLayerStructured interface 610 and the IStackLayerRaw interface 612 both allow a stack layer object to send and receive commands and data on behalf of the debugging tool 300. Thus, the IStackLayerStructured interface 610 is utilized by a protocol plug-in to send and receive commands and command arguments requested by the protocol manager 402. A command object is used to send and receive structured data to the stack layers of the device being tested 512 using the IStackLayerStructured interface 610. The stack IStackLayerRaw interface 612 allows a stack layer to send raw data provided by a user through the protocol manager 402.

Both structured commands and raw commands can be sent and received synchronously and asynchronously using methods in the stack layer structured command interface and the stack layer raw command interface. Further, both the stack layer structured command interface and the stack layer raw command interface have events that can be registered for receiving data back from a respective layer of the device being tested 512.

It is appreciated that the class structure of FIGS. 6A and 6B is exemplary and variations thereof are envisioned. Additionally, while the foregoing description provides an object oriented framework, other frameworks can also be implemented. Further, the methods implemented in each object of a plug-in will vary depending on the communication protocol being implemented. A developer will use the structures of the debugging tool 300 to develop a plug-in that is in accordance with the device being tested 512 and the plug-in is provided to the protocol plug-in datastore 412. Once the stack wrapper of a protocol plug-in is implemented, the debugging tool 300 can communicate to different layers of a device being tested 512 utilizing the communication protocol of the protocol plug-in.

Figure 7:
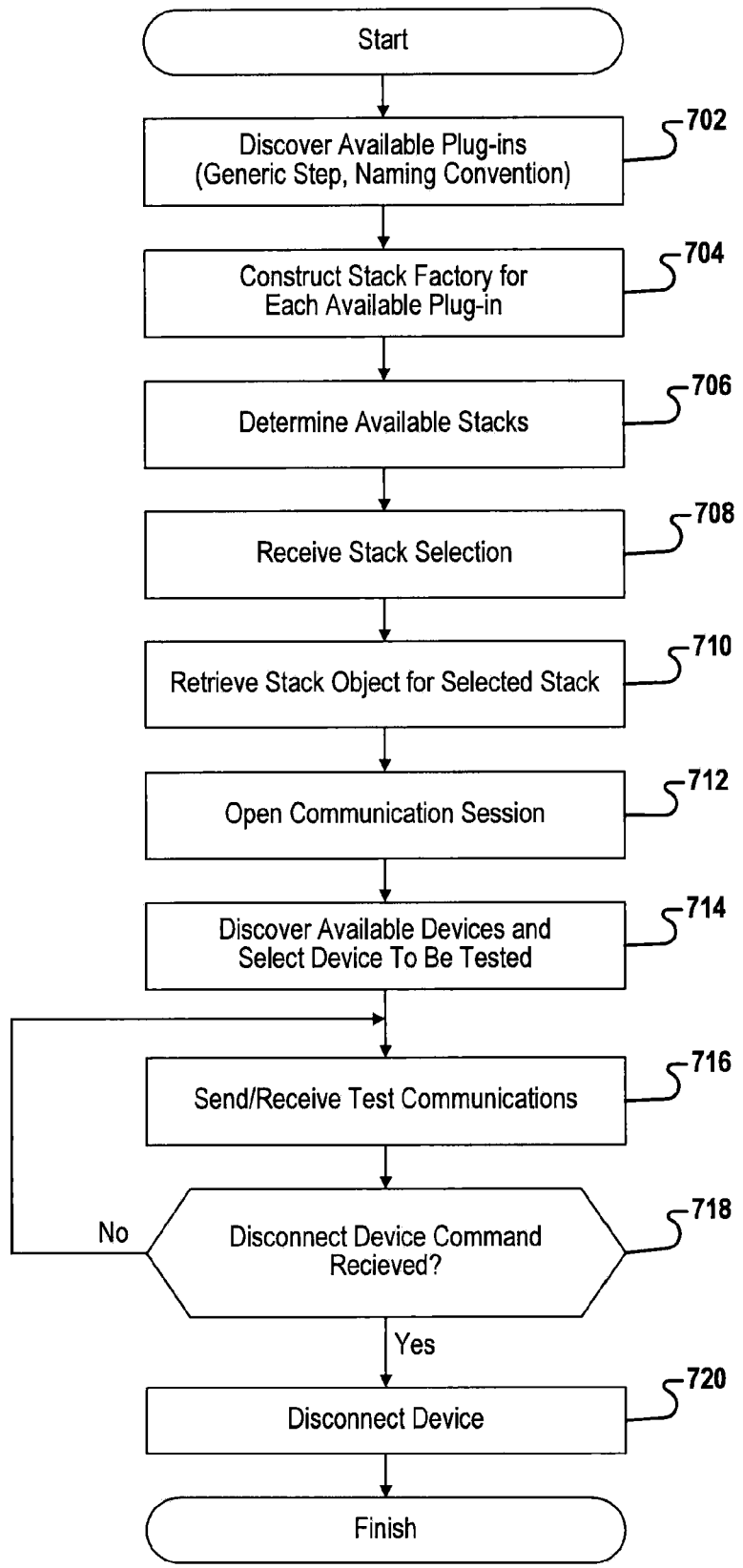
FIG. 7 is a flow chart illustrating an exemplary method that can be executed by the protocol manager.

FIG. 7 illustrates an exemplary method that can be executed by the debugging tool 300 to test a device. The method can be executed by a processor of a computer executing the debugging tool 300. When the debugging tool 300 is first initialized, the protocol manager 402 will discover available protocol plug-ins, as shown at step 702. The protocol manager 402 can achieve this in any suitable means. For example, the protocol manager 402 can search a list of CDFs in the CDF datastore 414, wherein each CDF can be associated to a protocol plug-in stored in the protocol plug-in datastore 412, or by using a reflection in an environment such as .NET. The available protocol plug-ins will each have an argument-free constructor for a class implementing a the IStackFactory interface. The stack broker 403 constructs all the objects it finds, as shown at step 704.

The stack broker 403 then finds the available stacks in a selected protocol plug-in using the available stacks method of the stack factory, e.g., IStackFactory.AvailableStacks( ), as shown at step 706. The available stacks method returns a list of the names of communication protocol stacks that the given protocol plug-in supports. The list is returned to the stack broker 403, which presents the list of available communication protocol stacks to the user. The user provides, and the debugging tool 300 receives a communication protocol stack selection, as shown at step 708. As previously noted, the user may be a developer operating a debugging tool 300, or an automated script or code. When the user has selected the name of the communication protocol stack, the stack broker 403 calls the get stack method of the stack factory containing the selected stack, e.g. IStackFactory.GetStack( ), which returns an implementation of a stack interface, as shown at step 710.

The stack broker 403 then calls the open session method on the stack object that was previously returned by the get stack method, as shown at step 712. The means by which a session is opened is dependent on the communication protocol being implemented by the plug-in. When a communication session is opened, the stack broker 403 provides the stack interface with an implementation of a stack logger interface that the stack broker 403 wants the stack interface 406 to use when logging data is passed between the device being tested 512 and the debugging tool 300. If the communication session was opened successfully, the stack interface instance 406 creates an object implementing a communication session interface, and returns the object to the stack broker 403.

When the stack interface 406 has returned the communication session object, the stack broker 403 calls the available devices method found in the communication session object, as shown at step 714. The available devices method calls its associated stack using whatever mechanism the associated stack supports to locate possible communication partners, i.e. the discovery mechanism defined by the communication protocol. The available devices method returns to the stack broker 403 a list of devices that are currently connected (or connectable) to the computer. It is noted that the list of available devices may have 0 or more members.

When the stack broker 403 receives a non-empty list of available devices, the stack broker 403 presents that list of available devices to the user. The user selects the device to be tested, and the stack broker 403 calls the connect method of the communication session object to request a connection to the specified device. The communication session object establishes a connection to the specified device using the mechanism supported by the communication protocol of the protocol plug-in. If the device has successfully connected to the stack interface 406, the communication session object will return an indication that a connection was successfully established to the stack broker 403.

Once a device is connected to the debugging tool 300, the debugging tool 300 can begin sending and receiving data to and from the device. The stack broker 403 requests from the stack object a list of the stack layer objects that are supported by the stack object. The stack object returns the list of supported stack layer objects to the stack broker 403, which presents the list to the user.

As mentioned above, the stack layers can be either "raw" or "structured." A "raw" stack layer implements the IStackLayerRaw interface. If the user knows the byte sequence that is to be sent to the device being tested 512, the user may simply send those bytes directly using a send asynchronously raw method, which is part of the stack layer raw command object. Similarly, the stack broker 403 can receive raw data packets using a send receive raw method, which is configured to send data packets to the device and wait for data packets to be received from the device being tested 512. The send asynchronously raw method and send receive raw method transmit bytes directly to the stack of the plug-in, which forwards the bytes to the device being tested 512 via the communication module that the device is connected to. The two methods differ only in whether the stack layer raw command implementation waits for a response from the device. When the send-receive raw transmissions method is called, the stack layer raw command object waits for predetermined amount of time for a response from the device being tested 512 before timing out. If a response is received, the stack layer raw command object returns the resulting bytes to the stack broker 403, which can then provide the results to the user or can log the results in the log file datastore 416.

The user can also instruct the debugging tool 300 to listen for raw data coming from the device being tested 512. The stack interface can listen for data on the stack layer raw command interface by providing a callback that accepts raw event arguments using a receive raw data-handler method, both of which are defined in the stack layer raw interface.

The user can also transmit structured commands using the IStackLayerStructured interface 610. To employ this interface, the user needs to be presented with a list of commands and arguments that the protocol plug-in and the device being tested 512 support. As will be discussed below, the commands can be provided by a command definition file (CDF). In some embodiments, the CDF can be an XML file associated with the protocol plug-in that lists the available commands and arguments. It is appreciated that other means of representing the available commands and arguments, including providing the commands and arguments in the protocol plug-in, are also possible. When the user wants to send data through a structured layer, the user can request, via the command interface 404, that the debugging tool 300 create a command object. The stack broker 403 will then call the create command method of the stack object, while providing byte codes for the command supplied by the user. If the selected command requires arguments, the stack broker 403 will use the overloaded create command that includes the argument values provided by the user.

As will be discussed below, the user can provide structured commands that support arguments having special data types such as floating point numbers, dates/times, and integers, via the command interface 404. The stack broker 403 utilizes the various convert methods to convert the special data types in accordance with the communication protocol of the device being tested 512. When the user has finished constructing the command and command arguments, the command is sent to the stack broker 403 via the protocol manager 402. The command is passed from the stack broker 403 to the protocol plug-in 506. The protocol plug-in 506, via its stack specific wrapper 520, converts a command defined in accordance with the stack interface to a command defined in accordance with the protocol defined in the protocol plug-in 506. As was described with respect to the IStackLayerRaw interface 612, the IStackLayerStructured interface 610 supports both asynchronous transmissions and send/receive transmissions.

The debugging tool 300 can be further configured to listen for data coming from the device being tested 512 at particular layers. Listening for data packets at a particular layer is performed by the objects implementing the IStackLayerStructured interface 610. The stack broker 403 can listen for data on an instantiated stack layer structured command object by providing a callback that accepts structured event arguments using a receive structured data handler method, both of which are such as specified by the ReceiveAsyncEventArgs class 616.

When the user is finished communicating with the device being tested 512, the stack broker 403 calls the disconnect method of the communication session object, which uses a mechanism in accordance with the communication protocol defined in the protocol plug-in to end a communication session, as shown at steps 718 and 720.

It is appreciated that the foregoing method is exemplary and variations thereof are within the scope of this disclosure. Further, the objects, methods, and arguments described above are exemplary as well.

Figure 8:
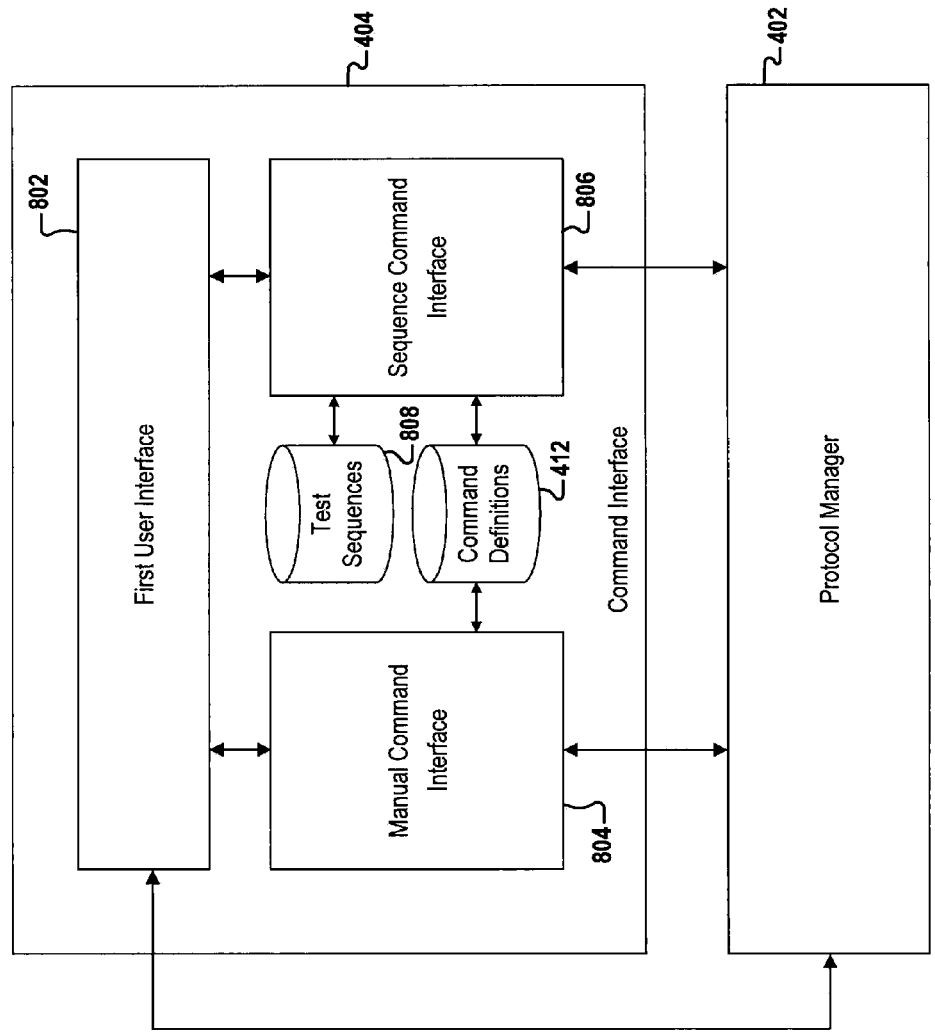
FIG. 8 is a block diagram illustrating exemplary components of the command interface of the debugging tool.

As was mentioned above, the debugging tool 300 includes a command interface that is configured to receive commands from a user and send the commands to the stack broker 403, which in turn sends the commands to a stack interface 406 for transmission to a device being tested 512, via a protocol plug-in 506. FIG. 8 illustrates an exemplary embodiment of the command interface 404.

The command interface 404 may include a first user interface 802, a manual command user interface 804, or a sequence command user interface 806. The command interface 404 further includes a command definition file datastore 414 in communication with the manual command user interface 804 and the sequence command user interface 806, and a test sequence datastore 808 in communication with the sequence command user interface 806.

The first user interface 802 is a user interface that allows a user to initially interact with the debugging tool 300. The first user interface 802 displays initial screens to the user, which allow the user to enter input indicating the type of testing that the user wants to perform. Initially, the first user interface 802 will present the user with an option of selecting the manual command user interface 804 or the sequence command user interface 806. Once the user selects one of the manual command user interface 804 and the sequence command user interface 806, the first user interface 802 will relinquish control to the selected manual command user interface 804 or 806.

The manual command user interface 804 is an interface that allows a user, e.g., developers or device testers, to communicate single manual commands to and from the protocol manager 402. The manual command user interface 804 is configured with a modular architecture which provides the user with access to a custom user interface for any device being tested 512. The manual command user interface 804 receives a protocol and/or a device type selection from the user and will launch a custom user interface corresponding to the selected device type and/or the selected protocol. The custom user interface will provide the user with elements for selecting layers of the selected communication protocol, a list of commands supported by the layer, and an input box for providing the input parameters associated with the selected command. When the user executes the command, the manual command user interface 804 will communicate the command to the protocol manager 402, which handles the command and provides the command to a device being tested 512 as described above.

The sequence command user interface 806 is an interface for defining, loading, editing, and saving sequences of test commands. The commands are defined in CDFs stored in the CDF datastore 414. The sequence command user interface performs several test sequence steps defined in templates or scripts, which can be stored in the test sequence datastore 808. The sequence command user interface 806 can execute the templates or scripts one at a time or in combination with other templates or scripts. In some embodiments, the sequence command user interface 806 will allow the user to pause, abort, insert breakpoints and perform stepping, as a command sequence is being executed. As will be described with respect to the manual command user interface 804, the sequence command user interface 806 uses the CDFs to generate commands which are then communicated to the protocol manager 402. The sequence command user interface 806 is further configured to allow a user to define a sequence of commands for testing. The sequence command user interface 806 then receives an instruction to execute the user defined sequence. The sequence command user interface 806 then communicates the commands to the protocol manager 402 and displays the results, if provided, to the user.

As previously discussed, the protocol manager 402 will receive a command from one of the manual command user interface 804 and the sequence command user interface 806. The protocol manager 402 will transmit the command via the stack broker 403, to a protocol plug-in 506 that generates one or more data packets corresponding to the command and in accordance with a communication protocol of a device being tested 512. The device being tested 512 may be configured to transmit a response back to the debugging tool 300, the response indicating an acknowledgement of a successful receipt of the command or with an error message. The protocol manager 402 can store the responses in the log file datastore 416 or can display the responses to the user via the manual command user interface 804 or the sequence command user interface 806.

Figure 9:
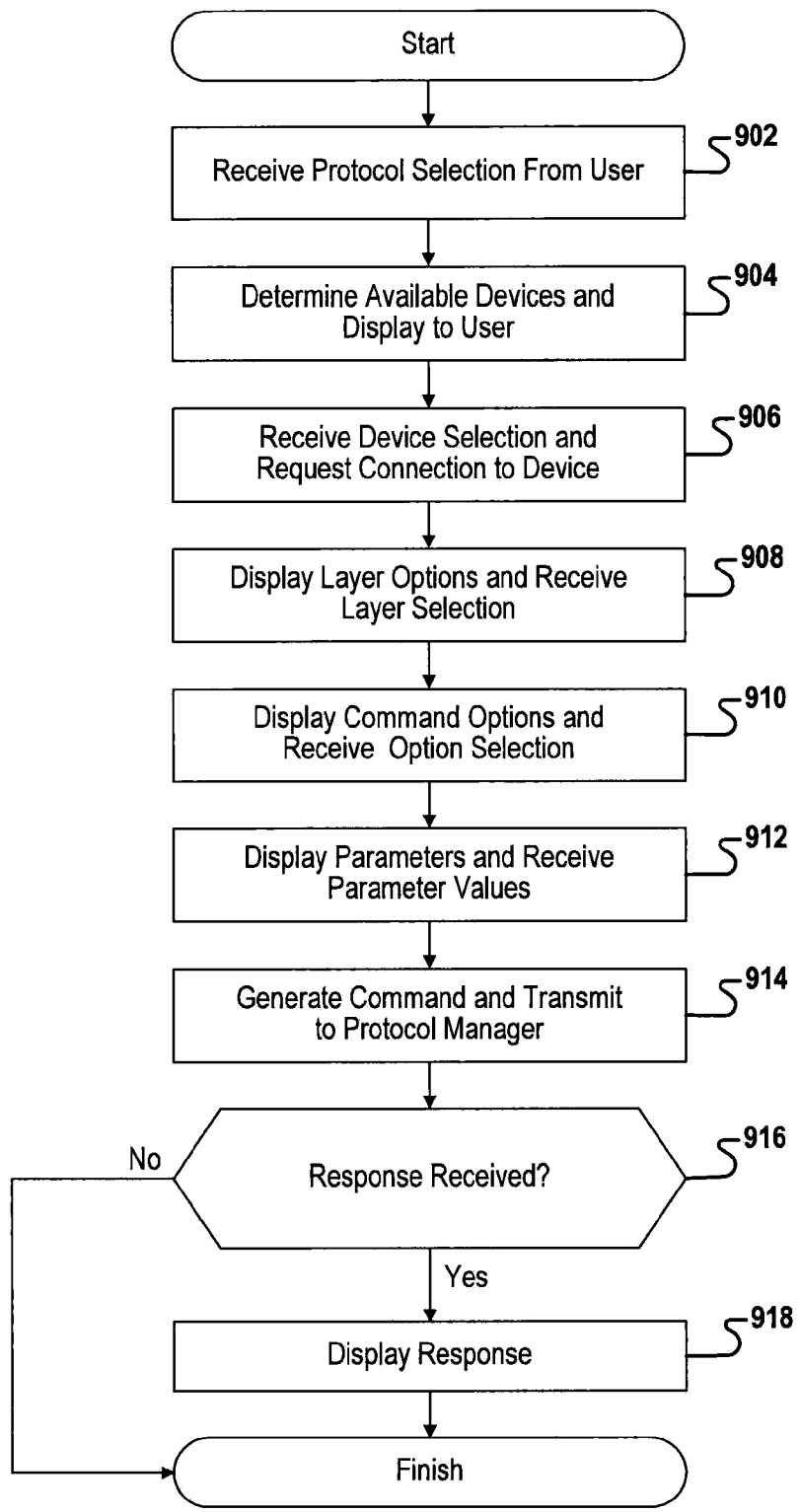
FIG. 9 is a flow chart illustrating an exemplary method that can be executed by the manual command user interface of the command interface.

FIG. 9 illustrates an exemplary method that can be executed by the manual command user interface 804. The method can begin executing once the user has selected to enter commands using the manual command user interface 804. As discussed with respect to the protocol manager 402, a list of available protocol plug-ins is determined by the protocol manager 402, which may search the CDF datastore 414 to determine a list of available CDFs. Each CDF will reference a corresponding protocol plug-in. Thus, a list of available protocols can be determined based on the command definition files stored in the command definition file datastore 414. Upon determining the list of available protocols, the manual command user interface 804 prompts the user to select a protocol from the list of available protocols. The user provides a protocol selection using the manual command user interface 804, as shown at step 902. It is appreciated that in some embodiments, the protocol selection can be provided to the first user interface 802. Upon receiving the user selection of a protocol, the manual command user interface 804 retrieves the corresponding command definition file from the command definition file datastore 414.

As discussed above, a protocol plug-in implements the stack interface 600. In the process of instantiating a protocol plug-in, a communication session supported by the protocol plug-in 506 is opened over the communication module 510. When the communication session is opened, the protocol plug-in 506 determines a list of devices available for communication. The list of available devices is displayed to the user, as shown at step 904. As will be discussed, the manual command user interface 804 may provide the user with a drop down menu of available devices. The user can use the drop down menu to provide a user device selection to the debugging tool 300. The manual command user interface 804 receives the user device selection and requests that the protocol manager 402 establish a connection with the selected device, as shown at step 906. The protocol manager 402 then establishes a connection with the selected device, i.e., the device being tested 512.

The manual command user interface 804 is configured to allow a user to provide instructions for a particular layer of a device's communication stack. Thus, the manual command user interface 804 displays a list of layer options and receives a layer selection from the user. As mentioned, the manual command user interface 804 retrieves a command definition file from the command definition file datastore 414. As will be described in greater detail below, the command definition file defines the layers of a protocol stack. The manual command user interface 804 determines the protocol layer options from the command definition file and displays the protocol layer options in a menu, e.g., a drop down menu. The user then provides a layer selection to the manual command user interface 804, as shown at step 908.

Once the user has selected a layer to communicate with, the manual command user interface 804 displays one or more command options to the user and will receive a command selection from the user, as shown at step 910. The manual command user interface 804 will retrieve the command options for the selected protocol layer from the command definition file and will display the selected commands to the user via a menu. The user will select the command from the menu. It is noted that the user may be further prompted to select a subcommand relating to the command. The manual command user interface 804 will then display an area for the user to provide one or more argument values for the command, as shown at step 912. The input area can include a field for each argument of the selected command. The user can then provide values for each argument command.

Upon the user providing the argument values, the manual command user interface 804 will generate a command for the protocol manager 402. The manual command user interface 804 can check the provided argument values to ensure that the arguments fall within an acceptable range defined in the command definition file. If the argument values are acceptable, the manual command user interface 804 generates a test command, as shown at step 914. An exemplary test command includes a stack selection indicating a protocol stack, a layer selection indicating a layer in the selected protocol stack, a command/subcommand selection indicating a command and possible subcommand for the selected layer, and zero or more argument values for the command/subcommand. The manual command user interface 804 communicates the test command to the protocol manager 402, which in turn communicates the test command to the appropriate protocol plug-in 506 via the stack broker 403 and the generic stack interface 406. The protocol plug-in 506 generates a data packet corresponding to the test command and communicates the data packet to the device being tested 512 via the physical transport of a corresponding communication module 510. It is noted that the manual command user interface 804 does not need to format the test command in accordance with any particular protocol and can generate in a language that is generic to the debugging tool 300.

If a response is received from the device being tested 512, the response is displayed by the manual command user interface 804. It is noted that the protocol plug-in 506 can decode the response from the communication-protocol-specific format to the generic language of the debugging tool 300. It is noted that the manual command user interface 804 can store the commands issued to a device being tested 512 and responses therefrom in the log file datastore 416.

Figure 10:
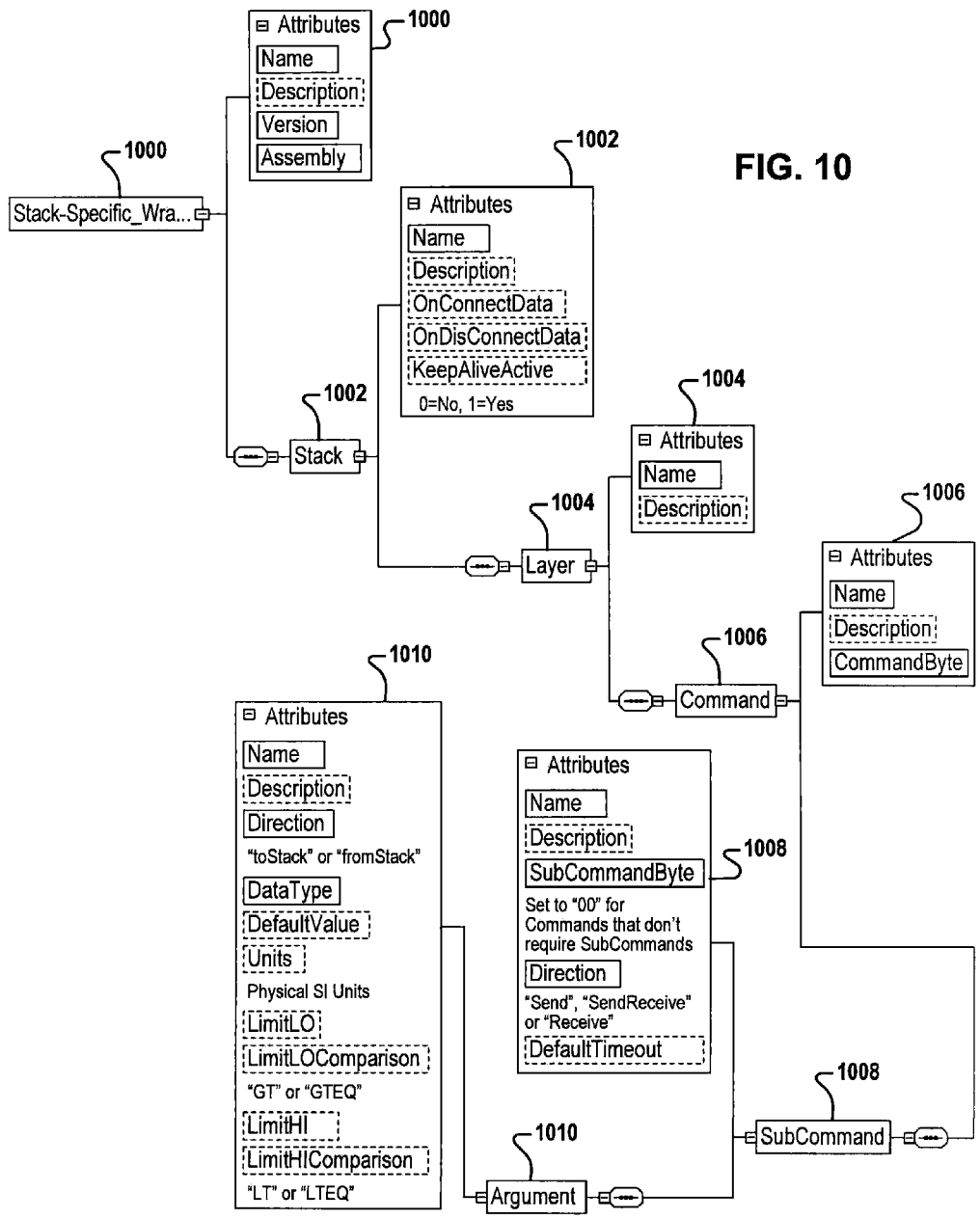
FIG. 10 is a schema diagram of an exemplary command definition file.

As referenced throughout the disclosure, a command definition file defines a set of commands for a device utilizing a specific layer of a specific communication protocol. An exemplary schema of a command definition file is provided in FIG. 10. As mentioned, each command definition file corresponds to a protocol plug-in. Thus, each command definition file corresponds to a protocol plug-in, and is defined with a top-level protocol plug-in entry 1000. The protocol plug-in entry 1000 can include a name and description of the protocol plug-in, as well as a version identifier and a reference to a protocol plug-in. The protocol stack-specific wrapper entry further includes one or more corresponding protocol stack entries 1002 associated thereto. A protocol stack entry 1002 includes a name of the protocol stack, a description of the protocol stack, and data regarding connecting to and disconnecting from a device.

As can be appreciated, a protocol stack is comprised of a plurality of layers. Thus, each protocol stack entry 1002 has a plurality of layer entries 1004 corresponding thereto. Each layer entry 1004 represents a layer of the protocol stack of stack entry 1002. Each layer entry 1004 can include a layer name and a description thereof. Each layer entry 1004 will also have one or more command entries 1006 associated to the layer. For instance, at the application layer of a communication protocol, a specific command supported by the application can be represented by a command entry 1006. A command entry 1006 can include a command name, a description, and a byte code representing the command.

Further, a command may include one or more subcommands. Thus, each command entry 1006 may include one or more corresponding subcommand entries 1008. A subcommand entry 1008 can include a name and description of the subcommand, a byte code representing the subcommand, and a direction flag indicating whether the subcommand is an incoming command, an outgoing command, or both. The subcommand may also include a timeout value associated therewith. It is noted that a command does not necessarily include a subcommand. In the instance a command does not include a subcommand, the byte code field of a subcommand entry can be set to a special value such as NULL or 00.

A command or subcommand can provide a device with one or more parameter values associated with the command or subcommand. Thus, each subcommand entry can have one or more parameter or argument entries 1010 associated therewith. An argument entry 1010 can have a name and description for the argument. The argument entry 1010 may further include a direction flag indicating whether the argument is sent to the stack or received from the stack. The argument entry can also include a data type of the argument, a default value of the data type, a unit type of the argument that indicates a physical SI unit type, and an allowable range for the argument values, i.e. an upper limit and a lower limit and whether the range is inclusive or exclusive.

It is appreciated that the foregoing description is exemplary and variations of the command definition schema exist. Provided in the appendix is an exemplary XML command definition file. It is appreciated that the command definition file provided is an example and not intended to be limiting.

Figure 11:
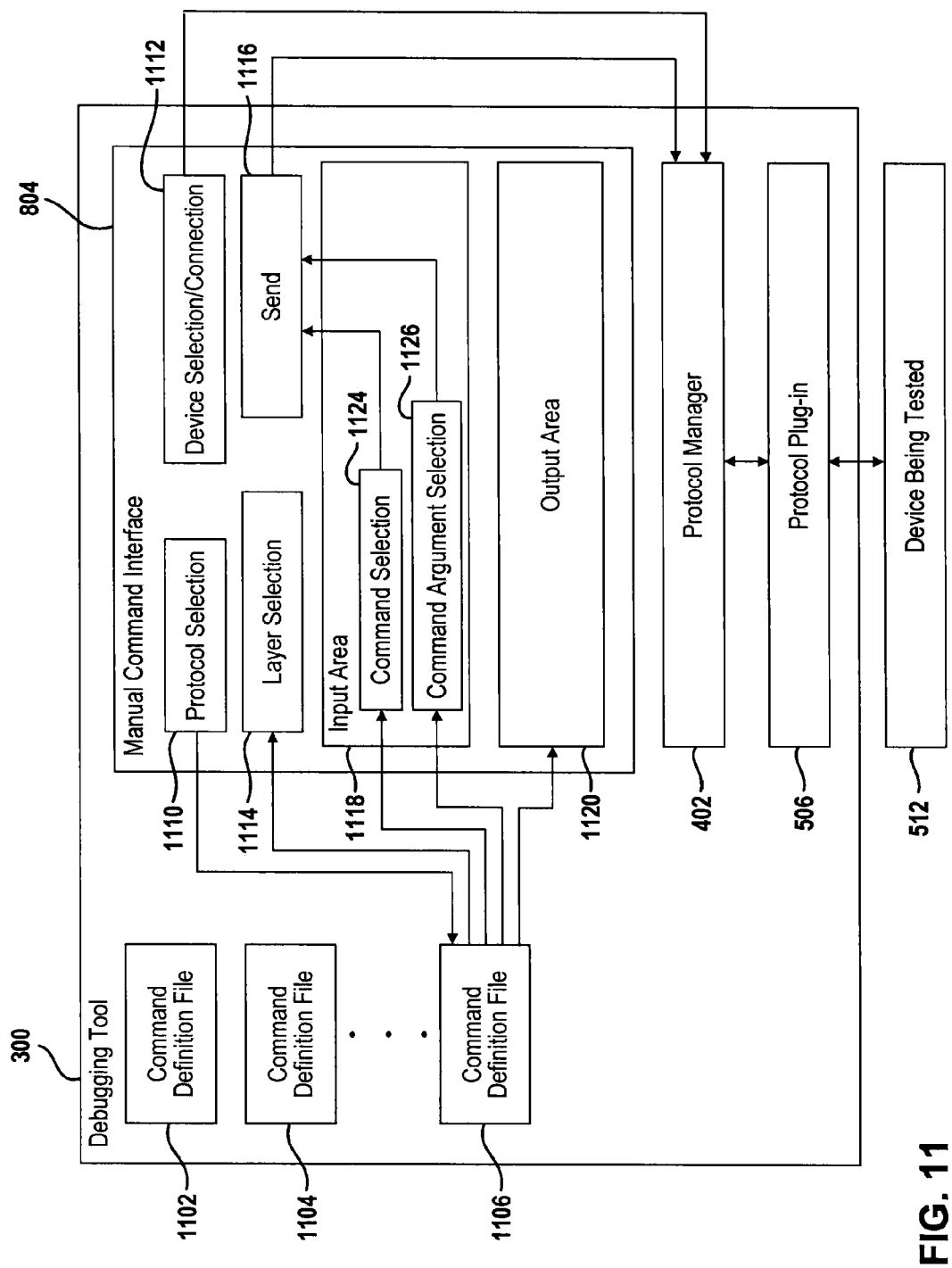
FIG. 11 is a block diagram illustrating exemplary components of the manual command user interface.

Referring now to FIG. 11, the exemplary components of the manual command user interface 804 are shown. The manual command user interface 804 includes a protocol selection area 1110, a device selection/connection area 1112, a layer selection area 1114, a send area 1116, an input area 1118, and an output area 1120. The input area can include a command selection area 1124 and a command argument selection area 1126. As described, the command definition file datastore 414 stores a plurality of command definition files 1102, 1104, and 1106.

As previously discussed, the debugging tool 300 allows a system developer to provide commands to a device being tested 512 via the protocol manager 402 and a protocol plug-in 506 that is protocol specific. The protocol plug-in 506 communicates with a device being tested 512 over an existing communication module 510 including a physical and logical transport, e.g., USB or Bluetooth®.

The protocol selection area 1110 provides the user with the ability to select a protocol. As previously discussed, the available protocols will correspond to the available command definition files 1102, 1104, and 1106. Thus, when the manual command user interface 804 begins operating, it searches in a command definition file datastore 414 for command definition files. The manual command user interface 804 populates the protocol selection area 1102 with the names of the protocols listed in the command definition files. The names of each protocol can be obtained from the protocol plug-in entry 1000 of each command definition file 1102, 1104, and 1106. For purposes of explanation and for example only, it is assumed that the user has selected the protocol corresponding to the Command Definition File 1106. When the user selects a protocol, the protocol selection is communicated to the protocol manager 402, and the protocol manager 402 opens a communication session using a stack interface 406 and returns a list of available devices. The device selection/connection area then displays the list of available devices to the user and receives a user selection and requests a connection. The user selection is communicated to the protocol manager 402, which makes the connection to the selected device 1150 via a communication module 510 corresponding to the selected protocol.

Once the device 1150 is connected to the debugging tool 300, the manual command user interface 804 populates the layer selection area 1114 with the available layers of the selected communication protocol. It is appreciated that the name of each layer can be obtained from the command definition file 1106 corresponding to the user protocol selection. The user can then select which protocol layer to debug by providing a layer selection at the layer selection area 1114.

In response to the layer selection, the manual command user interface 804 populates the command selection area 1124 with all the available commands for the selected layer. It is appreciated that the names of each command can be obtained from the selected command definition file 1106. The user then provides a command selection at the command selection area 1124. In response to the command selection, the manual command user interface 804 populates the command argument area 1126 with the arguments that must be supplied to generate the selected command. The command arguments are obtained from the selected command definition file 1106. The user can then enter values for the arguments the user wishes to provide in the command. Arguments that are not provided any values can be assigned a default value defined in the selected command definition file 1106.

Once the user has provided command argument values, the user can invoke the send element 1116 to send the command to the device being tested 512. The send element 1116 delivers the command and the argument values to the protocol manager 402. The protocol manager 402 passes the command to the protocol plug-in 506, which formats the command appropriately for the protocol, and transmits the command over the communication module 510.

The device being tested 512 receives the command, and may respond to the command. For example, the device being tested 512 may respond with an acknowledgement or an error message. When the device being tested 512 responds, the response is provided to the manual command user interface 804 and displayed in the output area 1120.

It is appreciated that the manual command user interface 804 may include additional elements and that variations of the manual command user interface 804 are contemplated.

Figure 12:
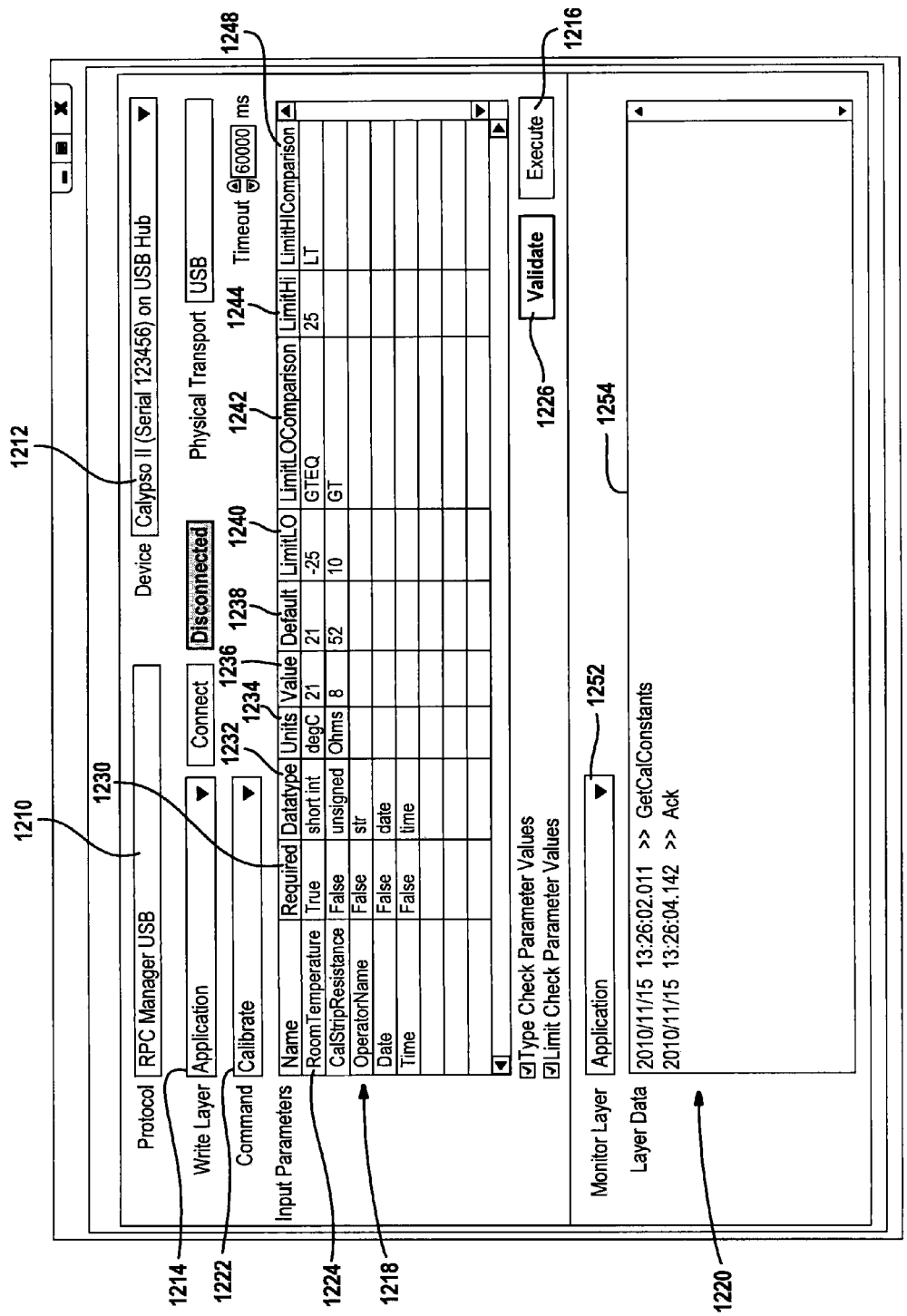
FIG. 12 is a drawing illustrating an exemplary screen shot of a customized screen displayed by the manual command user interface.

FIG. 12 illustrates an exemplary screen displayed by the manual command user interface 804. As can be observed, the user has provided a protocol selection of "RPC Manager USB" in a protocol selection area 1210. It is appreciated that the RPC Manager USB will have a protocol plug-in and a command definition file corresponding thereto. The user has selected a Calypso II device having a serial number 123456 for communication over a USB hub in the device selection area 1212. The user has selected the application layer in the layer selection area 1214.

Based on the user device and layer selections, the user is provided with a drop down menu 1222 for selecting a command type. In the example, the user has selected a calibrate command. The manual command user interface 804 displays a plurality of arguments corresponding to the calibrate command, including a room temperature argument and a calibration strip resistance. For each argument, the manual command user interface 804 can display whether an argument is required 1230, the data type of the argument 1232, the units of the argument 1235, a default value of the argument 1238, a lower limit of the argument value 1240, an indicator whether the lower limit is inclusive or exclusive 1242, an upper limit of the argument value 1244, and an indicator whether the upper limit is inclusive or exclusive 1246. Further, a field for the user to enter the argument value 1236 is also displayed.

Once the user has provided the arguments, the user can select the execute element 1216 to send the command. Further, the user can validate the argument values using the validate element 1226 before executing the command. The manual command user interface 804 will ensure that the argument values are permissible values. For example, the manual command user interface 804 will check if a proper data type was provided by the user and if the values fall within the ranges defined in the command definition file for the RPC Manager USB plug-in.

Once the user executes the test command, the device being tested 512 may respond to the test command. The response is displayed in the output area 1220. In the example, the user has selected the application layer in an output layer selection area 1252, thereby indicating to the manual command user interface 804 to display responses to the application layer from the device being tested 512 in a response area 1254.

It is appreciated that the foregoing is an exemplary screen shot and is not intended to be limiting. It is appreciated that any suitable arrangement of components can be implemented by the manual command user interface 804.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code, or a process executed by a distributed network of processors and storage in networked clusters or datacenters; other suitable components that provide the described functionality; or a combination of some or all of the above, such as in a system-on-chip. The term module may include memory (shared, dedicated, or group) that stores code executed by the one or more processors.

The term code, as used above, may include software, firmware, bytecode and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

APPENDIX

```xml
<?xml version="1.0"encoding="uff-8"?>
-<Roche_CITF_Stack-Specific_Wrapper Name='RPC Manager USB"Description="This is the IEEE 11073 Manager USB CITF
   Protocol"Assembly="IEEE11073"Version="1.0.0.0">
 - <Stack Name="IEEE11073MANAGERUSB"Description="IEEE 11073 Manager over USB"OnConnectData="50 00 01"
   OnDisconnectData=""KeepAliveTime="60"KeepAliveData="">
  - <Layer Name="IEEE11073Manager"Description="IEEE11073 Manager Layer">
   - <Command Name="IEEE_20601_CMD_ASSOCIATION_RESPONSE"CommandByte="00">
    -<SubCommand Name="IEEE_20601_CMD_ASSOCIATION_RESPONSE"SubCommandByte="01"
      Description="This command shall provide a response to the device's association request."
      Direction="Send">
      <Argument Name="Manager System ID"Description="Manager system ID as an 8 byte array"
       DataType="hexByteArray"Direction="toStack"LimitLO="8 bytes"LimitLOComparison="GTEQ"LimitHl="8
       bytes"LimitHlComparison="LTEQ"EnumType="0011"/>
     - <Argument Name="Response Type"Description='The response to an association request"
       DataType="unsignedShort"Direction="toStack"EnumType="0003">
       <enumList Name="Accepted"Value="0000"/>
       <enumList Name="RejectedPermanent"Value="0001"/>
       <enumList Name="RejectedTransient"Value="0002"/>
       <enumList Name="AcceptedUnknownConfig"Value="0003"/>
       <enumList Name="RejectedNoCommonProtocol"Value="0004"/>
       <enumList Name="RejectedNoCommonParameter"Value="0005"/>
       <enumList Name="RejectedUnknown"Value="0006"/>
       <enumList Name="RejectedUnauthorized"Value="0007"/>
       <enumList Name="RejectedUnsupportedAssociationVersion"Value="0008"/>
      </Argument>
     </SubCommand>
    </Command>
   - <Command Name="IEEE_20601_CMD_CONFIGURATION_RESPONSE"CommandByte="00">
    - <SubCommand Name="IEEE_20601_CMD_CONFIGURATION_RESPONSE"SubCommandByte="02"
      Description='This command shall provide a response to the device's configuration report."
      Direction="Send">
      <Argument Name="Agent Config ID"DataType="unsignedShort"Direction="toStack"EnumType="0003"/>
     - <Argument Name="Response Type"Description='The result of a configuration request"
       DataType="unsignedShort"Direction="toStack"EnumType="0003">
       <enumList Name="ConfigAccepted"Value="0000"/>
       <enumList Name="ConfigUnsupported"Value="0001"/>
       <enumList Name="ConfigUnknown"Value="0002"/>
      </Argument>
     </SubCommand>
    </Command>
   - <Command Name="IEEE_20601 CMD_ASSOCIATION_RELEASE_REQUEST"CommandByte="00">
    - <SubCommand Name="IEEE20601_CMD_ASSOCIATION_RELEASE_REQUEST"SubCommandByte="29"
      Description="This command shall request to release the association with the device."Direction="Send">
     - <Argument Name="Release Reason"Description="The reason for releasing association"
       DataType="unsignedShort"Direction="toStack"EnumType="0003">
       <enumList Name="Normal"Value="0000"/>
       <enumList Name="NoMoreConfigurations"Value="0001"/>
       <enumList Name="ConfigurationChanged"Value="0002"/>
      </Argument>
     </SubCommand>
    </Command>
   - <Command Name="IEEE_20601_CMD_SET_TIME_ACTION_REQUEST"CommandByte="00">
    - <SubCommand Name="IEEE_20601_CMD_SET_TIME_ACTION_REQUEST"SubCommandByte="0D"
      Description="This command shall provide a request for the set time action operation. This allows the
      manager system to set a real-time clock with the absolute time."Direction="Send">
      <Argument Name="Date Time"Description="Date Time as a byte array where a byte is used to represent the
       century, year, month, day, hour, minute, second, and fractions of a second (to the nearest hundredth of a
       second). Each field should be provided as a binary encoded decimal"
       DataType="hexByteArray"Direction="toStack"EnumType="0011"/>
     </SubCommand>
    </Command>
   - <Command Name="IEEE_20601_CMD_CONFIRMED_EVENTRESPONSE"CommandByte="00">
    - <SubCommand Name="IEEE_20601_CMD_CONFIRMED_EVENTRESPONSE"SubCommandByte="0F"
      Description="This command shall provide a confirmed event response. The confirmed event response is used to
```

APPENDIX-continued

```
    respond to a ROIV confirmed event report (typically used to respond to a scan report sent from an agent device)."
    Direction="Send">
      <Argument Name="Object Handle"Desciiption="The handle of the object associated with the response (should be
        the same object handle that was provided in the request)"DataType="unsignedShort"
        Direction="toStack"EnumType="0003"/>
    - <Argument Name="Event Type"Description="Event Type of the confirmation response."
        DataType="unsignedShort"Direction="toStack"EnumType="0003">
        <enumList Name="IEEE20601MDCNotifyFixedScanReport"Value="0D1D"/>
        <enumList Name="IEEE20601MDCNotifyVarScanReport"Value="0D1E"/>
        <enumList Name="IEEE20601MDCNotifyMPFixedScanReport"Value="0D1F"/>
        <enumList Name="IEEE20601MDCNotifyMPVarScanReport"Value="0D20"/>
        <enumList Name="IEEE20601MDCNotifyUnbufferedVarScanReport"Value="0D22"/>
        <enumList Name="IEEE20601MDCNotifyUnbufferedFixedScanReport"Value="0D23"/>
        <enumList Name="IEEE20601MDCNotifyUnbufferedGroupedScanReport"Value="0D24"/>
        <enumList Name="IEEE20601MDCNotifyUnbufferedMPVarScanReport"Value="0D25"/>
        <enumList Name="IEEE20601MDCNotifyUnbufferedMPFixedScanReport"Value="0D26"/>
        <enumList Name="IEEE20601MDCNotifyUnbufferedMPGroupedScanReport"Value="0D27"/>
        <enumList Name="IEEE20601MDCNotifyBufferedVarScanReport"Value="0D28"/>
        <enumList Name="IEEE20601MDCNotifyBufferedFixedScanReport"Value="0D29"/>
        <enumList Name="IEEE20601MDCNotifyBufferedGroupedScanReport"Value="0D2A"/>
        <enumList Name="IEEE20601MDCNotifyBufferedMPVarScanReport"Value="0D2B"/>
        <enumList Name="IEEE20601MDCNotifyBufferedMPFixedScanReport"Value="0D2C"/>
        <enumList Name="IEEE20601MDCNotifyBufferedMPGroupedScanReport"Value="0D2D"/>
      </Argument>
    </SubCommand>
  </Command>
- <Command Name="IEEE_20601_CMD_PM_STORE_CLEAR_ALL_SEGMENT_REQUEST"CommandByte="00">
  -<SubCommand Name="IEEE_20601_CMD_PM_STORE_CLEAR_ALL_SEGMENT_REQUEST"
    SubCommandByte="07" Description="This command shall provide a clear all segment request. The command sends a Clear
    Segments ROIV Confirmed Action request with a choice of All Segments. This allows the manager to delete the data currently
    stored in all PM-segments"Direction="Send">
      <Argument Name="Object Handle"Description="The handle of the PM-Store object for which segments are being cleared"
        DataType="unsignedShort"Direction="toStack"EnumType="0003"/>
    </SubCommand>
  </Command>
- <Command Name="IEEE_20601_CMD_PM_STORE_CLEAR_SEGMENTS_FROM_LIST_REQUEST"
    CommandByte="00">
    - <SubCommand Name="IEEE_20601_CMD_PM_STORE_CLEAR_SEGMENTS_FROM_LIST_REQUEST"
      SubCommandByte="08"Description=This command shall provide a clear segment request to clear the PM-segment data for
      the provided list of PM-Segment instances. The command sends a Clear Segments ROIV Confirmed Action request with a
      choice of Segment ID List. This allows the manager to delete the data currently stored for all PM-segments in the list"
      Direction="Send">
      <Argument Name="Segment List"Description="An array of PM-segment instance numbers"
        DataType="hexWordArray"Direction="toStack"EnumType="0004"/>
      <Argument Name="Object Handle"Description="The handle of the PM-Store object whose segments
        should be cleared" DataType="unsignedShort"Direction="toStack"EnumType="0003"/>
      <Argument Name="Segment Count"Description="The number of PM-segment instances provided in the
        segment list"DataType="unsignedShort"Direction="toStack"EnumType="0003"/>
    </SubCommand>
  </Command>
- <Command Name="IEEE_20601_CMD_STORE_CLEAR_SEGMENTS_BY_TIME_RANGE_REQUEST"
    CommandByte="00">
  - <SubCommand Name="IEEE_20601__CMD_PM_STORE_CLEAR_SEGMENTS_BY_TIME_RANGE_REQUEST"
    SubCommandByte="09"Description="This command shall provide a clear segment request based on time
    range. The command sends a Clear Segments ROIV Confirmed Action request with a choice of Absolute
    Time Range. This allows the manager to request a deletion of the data currently stored in all appropriate
    PM-segments that fall within the time range"Direction="Send">
    <Argument Name="From Time"Description="The lower bounds of the time range expressed in absolute
      time"DataType="hexByteArray"Direction="toStack"EnumType="0011"/>
    <Argument Name="To Time"Description='The upper bounds of the time range expressed in absolute
      time"DataType="hexByteArray"Direction="toStack"EnumType="0011"/>
    <Argument Name="Object Handle"Description="The handle of the PM-Store object whose segments are
      being cleared"DataType="unsignedShort"Direction="toStack"EnumType="0003"/>
  </SubCommand>
</Command>
- <Command
  Name="IEEE_20601_CMD_PM_STORE_CLEAR_SEGMENTS_BY_BASE_OFFSET_TIME_RANGE_REQUEST"
  CommandByte="00">
  - <SubCommand
    Name="IEEE 20601_CMD_PM_STORE_CLEAR_SEGMENTS_BY_BASE_OFFSET_ TIME_RANGE_REQUEST"
    SubCommandByte="0A"Description="This command shall provide a clear all segment request based onthe base offset
    time range. The command sends a Clear Segments ROIV Confirmed Action request with a choice of base offset time range.
```

APPENDIX-continued

This allows the manager to request a deletion of the data currently stored in all appropriate PM-segments that fall within the base offset time range"Direction="Send">
<Argument Name="From Seconds"Description="Part of the base time offset datatype, this argument helps to express the lower bounds of the time range. The argument represents the number of seconds since midnight of the 1st of January 1900"DataType="unsignedInt"Direction="toStack" EnumType="0012"/>
<Argument Name="From Fraction"Description="Part of the base time offset datatype, this argument helps to express the lower bounds of the time range. The argument represents the fraction of x/65536ths of a second" DataType="unsignedShort"Direction="toStack" EnumType="0003"/>
<Argument Name="From Offset"Description="Part of the base time offset datatype, this argument helps to express the lower bounds of the time range. The argument represents the difference in minutes between the base time and the local time"DataType="short"Direction="toStack"EnumType="0002"/>
<Argument Name="To Seconds"Description="Part of the base time offset datatype, this argument helps to express the upper bounds of the time range. The argument represents the number of seconds since midnight of the 1st of January 1900"DataType="unsignedInt"Direction="toStack"EnumType="0012"/>
<Argument Name="To Fraction"Description="Part of the base time offset datatype, this argument helps to express the upper bounds of the time range. The argument represents the fraction of x/65536ths of a second"DataType="unsignedShort"Direction="toStack"EnumType="0003"/>
<Argument Name="To Offset"Description="Part of the base time offset datatype, this argument helps to express the upper bounds of the time range. The argument represents the difference in minutes between the base time and the local time"DataType="short"Direction="toStack"EnumType="0002"/>
<Argument Name="Object Handle"Description="The handle of the PM Store object whose segments are being cleared"DataType="unsignedShort"Direction="toStack"EnumType="0003"/>
</SubCommand>
</Command>
- <Command Name="IEEE_20601_CMD_TRIGGER_SEGMENT_DATA_TRANSFER_REQUEST"CommandByte="00">
  - <SubCommand Name="IEEE_20601_CMD_TRIGGER_SEGMENT_DATA_TRANFER_REQUEST" SubCommandByte="0D"Description="This command shall provide a trigger segment data transfer request. This allows the manager to start the transfer of the Fixed-Segment-Data attribute of a specified PM-segment"Direction="Send">
    <Argument Name="Object Handle"Description="The handle of the PM-Store object" DataType="unsignedShort"Direction="toStack"EnumType="0003"/>
    <Argument Name="Segment ID"Description='The PM-segment Instance Number" DataType="unsignedShort"Direction="toStack"EnumType="0003"/>
  </SubCommand>
</Command>
- <Command Name="IEEE_20601_CMD_PM_STORE_SEGMENT_DATA_EVENT_RESPONSE"CommandByte="00">
  - <SubCommand Name="IEEE_20601_CMD_PM_STORE_SEGMENT_DATA_EVENT_RESPONSE" SubCommandByte="0B"Description="This command shall provide a response to a segment data event report sent by an agent device."Direction="Send">
    <Argument Name="Segment Entry Count"Description='The total count of segment data event reports being sent (should be the count reported in the event report sent by the agent.)" DataType="unsignedInt"Direction="toStack"EnumType="0012"/>
    <Argument Name="Segment Entry Index"Description="The index of the segment data event report (should be the index reported in the event report sent by the agent)"DataType="unsignedInt" Direction="toStack"EnumType="0012"/>
    <Argument Name="Object Handle"Description="The handle of the PM-Store object to which the data pertains"DataType="unsignedShort"Direction="toStack"EnumType="0003"/>
    <Argument Name="Segment ID"Description="The segment Id of the PM-segment for which data was reported"DataType="unsignedShort"Direction="toStack"EnumType="0003"/>
    <Argument Name="Segment Event Status"Description="A status to send back to the agent (SegmEvtStatus)"DataType="unsignedShort"Direction="toStack"EnumType="0003"/>
  </SubCommand>
</Command>
- <Command Name="IEEE_20601_CMD_PM_STORE_GET_ALL_SEGMENT_INFO_REQUEST"CommandByte="00">
  - <SubCommand Name="IEEE_20601_CMD_PM_STORE_GET_ALL_SEGMENT_INFO_REQUEST" SubCommandByte="03"Description='This command shall provide a get all segment info request. The command sends a get segment info ROIV Confirmed Action with a choice of All Segments. This allows the manager to retrieve PM-segment attributes of one or more PM-segments, with the exception of the Fixed-Segment-Data attribute."Direction="Send">
    <Argument Name="Object Handle"Description="The handle of the PM-Store object whose PM-segment data is being retrieved"DataType="unsignedShort"Direction="toStack"EnumType="0003"/>
  </SubCommand>
</Command>
- <Command Name="IEEE_20601_CMD_PM_STORE_GET_SEGMENT_INFO_BY_ID_LIST_REQUEST" CommandByte="00">
  - <SubCommand Name="IEEE_20601_CMD_PM_STORE_GET_SEGMENT_INFO_BY_ID_LIST_REQUEST" SubCommandByte="04"Description="This command shall provide a get segment info by ID list request. The command sends a get segment info ROIV Confirmed Action with a choice of Segment ID List. This allows the manager to retrieve PM-segment attributes of one or more PM-segments provided in the Segment ID List."Direction="Send">
    <Argument Name="Segment List"Description="An array of PM-segment instance numbers" DataType="hexWordArray"Direction="toStack"EnumType="0004"/>
    <Argument Name="Object Handle"Description='The handle of the PM-Store object whose segment attributes are being retrieved."DataType="unsignedShort"Direction="toStack"EnumType="0003"/>
    <Argument Name="Segment Count"Description="The number of PM-segment instances provided in the segment list"DataType="unsignedShort"Direction="toStack"EnumType="0003"/>

APPENDIX-continued

```
    </SubCommand>
  </Command>
- <Command Name="IEEE_20601_CMD _PM_STORE_GET_SEGMENT_INFO_BY_ABS_TIME_RANGE_REQUEST"
  CommandByte="00">
  - <SubCommand
    Name="IEEE_20601_CMD_PM_STORE_GET_SEGMENT_INFO_BY_ABS_TIME_RANGE_REQUEST"
    SubCommandByte="05"Description="This command shall provide a get segment info by absolute time
    range request. The command sends a get segment info ROW Confirmed Action with a choice of Absolute
    Time Range. This allows the manager to retrieve PM-segment attributes of each of the PM-segments that
    fall within the absolute time range"Direction="Send">
      <Argument Name="From Time"Description='The lower bounds of the time range expressed in absolute
        time"DataType="hexByteArray"Direction="toStack"EnumType="0011"/>
      <Argument Name="To Time"Description=The upper bounds of the time range expressed in absolute
        time"DataType="hexByteArray"Direction="toStack"EnumType="0011"/>
      <Argument Name="Object Handle"Description='The handle of the PM-Store object whose segments are
        being retrieved"DataType="unsignedShort"Direction="toStack"EnumType="0003"/>
    </SubCommand>
  </Command>
- <Command
  Name="IEEE_20601_CMD_PM_STORE_GET_SEGMENT_INFO_BY_BASE_OFFSET_TIME_RANGE_REQUEST"
  CommandByte="00">
  - <SubCommand
    Name="IEEE_20601_CMD_PM_STORE_GET_SEGMENT_INFO_BY_BASE_OFFSET_TIME_RANGE_REQUEST"
    SubCommandByte="06"Description="This command shall provide a get segment info by a base offset time
    range request. The command sends a get segment info ROIV Confirmed Action with a choice of Base
    Offset Time Range. This allows the manager to retrieve PM-segment attributes of each of the PM-
    segments that fall within the base offset time range"Direction="Send">
      <Argument Name="From Seconds"Description="Part of the base time offset datatype, this argument
        helps to express the lower bounds of the time range. The argument represents the number of
        seconds since midnight of the 1st of January 1900"DataType="unsignedInt"Direction="toStack"
        EnumType="0012"/>
      <Argument Name="From Fraction"Description="Part of the base time offset datatype, this argument helps
        to express the lower bounds of the time range. The argument represents the fraction of x/65536ths
        of a second"DataType="unsignedShort"Direction="toStack"EnumType="0003"/>
      <Argument Name="From Offset"Description="Part of the base time offset datatype, this argument helps
        to express the lower bounds of the time range. The argument represents the difference in minutes
        between the base time and the local time"DataType="short"Direction="toStack"EnumType="0002"/>
      <Argument Name="To Seconds"Description="Part of the base time offset datatype, this argument helps
        to express the upper bounds of the time range. The argument represents the number of seconds
        since midnight of the 1st of January 1900"DataType="unsignedInt"Direction="toStack"
        EnumType="0012"/>
      <Argument Name="To Fraction"Description="Part of the base time offset datatype, this argument helps to
        express the upper bounds of the time range. The argument represents the fraction of x/65536ths of a
        second"DataType="unsignedShort"Direction="toStack"EnumType="0003"/>
      <Argument Name='To Offset"Description="Part of the base time offset datatype, this argument helps to
        express the upper bounds of the time range. The argument represents the difference in minutes
        between the base time and the local time"DataType="short"Direction="toStack"EnumType="0002"/>
      <Argument Name='Object Handle"Description="The handle of the PM-Store object whose segments are
        being retrieved"DataType="unsignedShort"Direction="toStack"EnumType="0003"/>
    </SubCommand>
  </Command>
- <Command Name="IEEE_20601_CMD_SET_BASE_OFFSET_TIME_ACTION_REQUEST"CommandByte="00">
  - <SubCommand Name="IEEE_20601_CMD_SET_BASE_OFFSET_TIME_ACTION_REQUEST"
    SubCommandByte="0E"Description='This command shall provide a set base offset time action request. This
    allows the manager system to set a real-time clock with a base time and the offset in minutes to the local
    time."Direction="Send">
      <Argument Name="Seconds"Description="This argument represents the number of seconds since
        midnight of the 1st of January 1900"DataType="unsignedInt"Direction="toStack"EnumType="0012"/>
      <Argument Name="Fraction"Description="This argument represents the fraction of x/65536ths of a
        second"DataType="unsignedShort"Direction="toStack"EnumType="0003"/>
      <Argument Name="Offset"Description="This argument represents the difference in minutes between the
        base time and the local time"DataType="short"Direction="toStack"EnumType="0002"/>
    </SubCommand>
  </Command>
- <Command Name="IEEE_20601_CMD_DATA_REQ_ACTION_REQUEST"CommandByte="00">
  - <SubCommand Name"IEEE_20601_CMD_DATA_REQ_ACTION_REQUEST"SubCommandByte="10"
    Description="The command will provide a data req action request. This allows the manager system to
    enable or disable measurement data transmission from the agent, where the agent sends corresponding
    scan reports based on the managers request"Direction="Send">
    <Argument Name="Object Handle"Description="The handle of the object making the request"
      DataType="unsignedShort"Direction="toStack EnumType="0003"/>
    <Argument Name="Data Request ID"Description="An Id for the data request. It is used to differentiate
      responses from mulitple data requests to the same agent (if applicable)"DataType="unsignedShort"
      Direction="toStack"EnumType="0003"/>
    <Argument Name="Data Req Mode"Description="Mode flags for the data request that determine the start
      request mode, the object scope, and/or the stop request mode"DataType="unsignedShort"
      Direction="toStack"EnumType="0003"/>
    <Argument Name="Relative Time"Description="The relative time of the request"DataType="unsignedlnt"
      Direction="toStack"EnumType="0012"/>
```

APPENDIX-continued

```xml
        <Argument Name="Person ID" Description="The identifier of the person associated with the data"
            DataType="unsignedShort" Direction="toStack" EnumType="0003"/>
        <Argument Name="Class ID" Description="The class identifier that defines the class of objects to report"
            DataType="unsignedShort" Direction="toStack" EnumType="0003"/>
        <Argument Name="Count" Description="The number of handles provided in the handle list"
            DataType="unsignedShort" Direction="toStack" EnumType="0003"/>
        <Argument Name="Handle List" Description="An array of attribute handles for which data should be
            retrieved" DataType="hexByteArray" Direction="toStack" EnumType="0011"/>
      </SubCommand>
    </Command>
  -<Command Name="IEEE_20601_CMD_ABORT_REQUEST" CommandByte="00">
    + <SubCommand Name="IEEE_20601_CMD_ABORT_REQUEST" SubCommandByte="2A" Description="This
        command shall send an abort request." Direction="Send">
    </Command>
    <Command Name="IEEE_20601_CMD_ERROR_RESPONSE" CommandByte="00">
      -<SubCommand Name="IEEE_20601_CMD_ERROR_RESPONSE" SubCommandByte="2B" Description="This
          command shall send an error response. An error response can be used to respond to any request in the
          event of an error in processing the request" Direction="Send">
        <Argument Name="Parameters" Description="The parameters associated with the error"
            DataType="hexByteArray" Direction="toStack" EnumType="0011"/>
        <Argument Name="Invoke ID" Description="The Invoke Id for the response (should be the same as the
            request)" DataType="unsignedShort" Direction="toStack" EnumType="0003"/>
        - <Argument Name="Error Value" Description="The error code for the type of error that occured"
            DataType="unsignedShort" Direction="toStack" EnumType="0003">
          <enumList Name="NoSuchObjectInstance" Value="0001"/>
          <enumList Name="AccessDenied" Value="0002"/>
          <enumList Name="NoSuchAction" Value="0009"/>
          <enumList Name="InvalidObjectInstance" Value="0011"/>
          <enumList Name="ProtocolViolation" Value="0017"/>
          <enumList Name="NotAllowedByObject" Value="0018"/>
          <enumList Name="ActionTimedOur Value="0019"/>
          <enumList Name="ActionAborted" Value="001A"/>
        </Argument>
      </SubCommand>
    </Command>
    <Command Name="IEEE_20601_CMD_REJECT_RESPONSE" CommandByte="00">
      - <SubCommand Name="IEEE_20601_CMD_REJECT_RESPONSE" SubCommandByte="2C" Description="This
          command shall send a reject response." Direction="Send">
        <Argument Name="Invoke ID" Description="The Invoke Id for the response (should be the same as the
            request)" DataType="unsignedShort" DirectionetoStack" EnumType="0003"/>
        <Argument Name="Reject Value" Description="The reason for rejection (RorjProblem)"
            DataType="unsignedShort" Direction="toStack" EnumType="0003"/>
      </SubCommand>
    </Command>
    <Command Name="IEEE_20601_CMD_ROIV_GET_SERVICE_REQUEST" CommandByte="00">
      <SubCommand Name="IEEE_20601_CMD_ROIV_GET_SERVICE REQUEST" SubCommandByte="2D"
          Description="This command shall send an ROIV get service request. This allows the manager to send a get
          request to a peer device." Direction="Send">
        <Argument Name="Attribute List" Description="A list of attributes being requested. An empty attribute list
            and a count of zero implies all attributes are being requested" DataType="hexByteArray"
            Direction="toStack" EnumType="0011"/>
        <Argument Name="Object Handle" Description="Handle of the object instance for which the Get Service
            is requested" DataType="unsignedShort" Direction="toStack" EnumType="0003"/>
        <Argument Name="Count" Description="The count of attributes being requested. An empty attribute list
            and a count of zero implies all attributes are being requested" DataType="unsignedShort"
            Direction="toStack" EnumType="0003"/>
      </SubCommand>
    </Command>
  </Layer>
</Stack>
</Roche_CITF_Stack-Specific_Wrapper>
```

What is claimed is:

1. A too for testing a plurality of different devices having different device types, the plurality of different device types having different communication protocols associated therewith, the tool comprising:

a plurality of communication components, each communication component having a different physical transport for communicating with one or more of the plurality of different device types, each communication component being configured to communicate using at least one of the plurality of different communication protocols; and a computing device comprising a processor configured to execute:

a command interface configured to receive a selection of a given command definition the and, in response to receiving the selection of the given command definition file, retrieve the given command definition the from a command definition datastore and pass the given command definition the to a protocol manager, where the given command definition file defines a set of commands for a device being tested and a communication protocol for the device being tested;

the protocol manager configured to receive given command definition the from the command interface and, in response to receiving the given command definition file, retrieve a protocol plug-in from a plurality of available protocol plug-ins, each protocol plug-in of the plurality of available protocol plug-ins supporting one of the different communication protocols;

a stack broker configured to receive the retrieved protocol plug-in from the protocol manager and, in response to receiving the retrieved protocol plug-in, instantiates the retrieved protocol plug-in, wherein each protocol plug-in from the plurality of available protocol plug-ins implements a common stack interface, the stack broker being configured to:

a) when commanded over the common stack interface, open a communication session with a device being tested over one of the plurality of communication components, and b) when commanded over the common stack interface, generate one or more data packets intended for the device being tested according to the communication protocol supported by the protocol plug-in;

the protocol manager being further configured to receive a command for the test device, along with at least one parameter value, as defined in the given command definition file and passes the command to the stack broker wherein the instantiated protocol plug-in:

i) receives the command and the at least one parameter value, ii) converts the command to a command defined within the instantiated protocol plug-in, iii) generates one or more packets corresponding to the command defined within the instantiated protocol plug-in for the device being tested according to the communication protocol corresponding to the instantiated protocol plug-in, and iv) communicates the one or more packets to the device being tested using the open communication session; and wherein the protocol manager is further configured to store the retrieved command and response data corresponding to response packets received from the device being tested in a log the datastore.

2. The tool of claim 1 further comprising a command interface that is configured to:

A) receive a communication protocol selection and a device selection,

B) display a set of selectable commands for the selected device,

C) receive a command selection,

D) display one or more arguments for the command selection, and

E) receive the arguments for the command selection.

3. The tool of claim 2 wherein the command interface retrieves a command for the selected device and provides the command to the protocol manager, wherein the protocol manager provides the command to the instantiated protocol plug-in in accordance with the common stack interface.

4. The tool of claim 2 wherein the command interface is further configured to retrieve a command definition file corresponding to the protocol selection, wherein the retrieved command definition file defines the selectable commands and arguments for the selectable commands.

5. The tool of claim 4 wherein the command interface is further configured to display a set of testable layers indicating different layers of the communication protocol corresponding to the retrieved command definition file and the instantiated protocol plug-in, and to receive a layer selection, wherein the set of selectable commands are directed to the selected layer.

6. The tool of claim 1 further comprising a protocol plug-in datastore that stores a plurality of protocol plug-ins.

7. The tool of claim 6 wherein a developer provides a new protocol plug-in for storage in the protocol plug-in datastore, such that the new protocol plug-in is included in the available protocol plug-ins after the new protocol plug-in has been provided to the protocol plug-in datastore, and wherein the new protocol plug-in is configured to generate data packets intended for a new device being tested in accordance with a new communication protocol.

8. The tool of claim 7 wherein the developer provides a command definition file corresponding to the new protocol plug-in, wherein the new command definition file defines commands that can be communicated to the new device being tested.

9. The tool of claim 1 wherein the protocol plug-in is further configured to:

v) receive response packets from the device being tested, vi) generate response data by decoding the response packets according to the communication protocol corresponding to the instantiated protocol plug-in, and vii) providing the response data to the protocol manager.

10. The tool of claim 9 wherein the response data is at least one of displayed to the user and stored in a log file.

11. A method for configuring a tool for testing a plurality of different devices having different device types, the plurality of different devices each having a different communication protocol associated therewith, and the tool including a plurality of communication components, each communication component having a different physical transport for communicating with one or more of the plurality of different device types, each communication component being configured to communicate using at least one of the plurality of different communication protocols, the method comprising:

receiving, via a command interface, a selection of a given command definition file;

retrieving the given command definition file from a command definition datastore, where the retrieval is in response to receiving the selection of the given command definition file and a communication protocol is associated with the given command definition file;

retrieving a protocol plug-in from a plurality of protocol plug-ins, wherein the retrieval is in response to retrieving the given command definition file and each protocol plug-in of the plurality of available protocol plug-ins supporting one of the different communication protocols;

receiving a protocol selection corresponding to one of the available protocol plug-ins, wherein each protocol plug-in implements a common stack interface;

instantiating a protocol plug-in corresponding to the protocol selection;

receiving a command, for the device being tested, from a command definition file datastore;

communicating the retrieved command to the protocol manager;

receiving the command for a test device and at least one parameter value corresponding to the command;

selecting the protocol selection based on the command;

retrieving the protocol plug-in corresponding to the protocol selection from a protocol plug-in datastore;

storing the retrieved command and response data corresponding to response packets received from the device being tested in a log file datastore; and providing the instantiated protocol plug-in with the command and the at least one parameter value, wherein the instantiated protocol plug-in is configured to perform:
- i) opening a communication session with a device being tested over one of the plurality of communication components
- ii) receiving the command and the at least one parameter value,
- iii) converting the command to a command defined within the instantiated protocol plug-in,
- iv) generating one or more data packets corresponding to the command defined within the instantiated protocol plug-in for the device being tested according to the communication protocol corresponding to the instantiated protocol plug-in, and
- v) communicating the one or more packets to the device being tested using the open communication session;

wherein the steps of determining, receiving a protocol selection, receiving a command for a test device, instantiating, and providing are computer executed instructions stored on memory and executed by a processor.

12. The method of claim 11 further comprising:
receiving a communication protocol selection and a device selection,
displaying a set of selectable commands for the selected device,
receiving a command selection,
displaying one or more arguments for the command selection, and
receiving the arguments for the command selection.

13. The method of claim 12 further comprising generating a command for the selected device and providing the command to the instantiated protocol plug-in, the command being provided in accordance with the common stack interface.

14. The method of claim 12 further comprising retrieving a command definition file based on the protocol selection and retrieving a protocol plug-in based on the retrieved command definition file, wherein the retrieved command definition file defines the selectable commands and arguments for the selectable commands, and wherein the instantiated protocol plug-in is the retrieved protocol plug-in.

15. The method of claim 14 further comprising:
displaying to a user a set of testable layers indicating different layers of the communication protocol corresponding to the retrieved command definition file and the instantiated protocol plug-in; and
receiving a layer selection, wherein the set of selectable commands are directed to the selected layer.

16. The method of claim 11 further comprising storing a plurality of protocol plug-ins in a protocol plug-in datastore, wherein the available protocol plug-ins are stored in the protocol plug-in datastore.

17. The method of claim 16 further comprising receiving a new protocol plug-in from a developer for storage in the protocol plug-in datastore, such that the new protocol plug-in is included in the available protocol plug-ins after the new protocol plug-in has been provided to the protocol plug-in datastore, and wherein the new protocol plug-in is configured to generate data packets intended for a new device being tested in accordance with a new communication protocol.

18. The method of claim 17 further comprising receiving a command definition file corresponding to the new protocol plug-in from the developer, wherein the new command definition file defines commands that can be communicated to the new device being tested.

19. The method of claim 11 wherein the instantiated protocol plug-in is further configured to perform:
- vi) receiving response packets from the device being tested,
- vii) generating response data by decoding the test packets according to the communication protocol corresponding to the instantiated protocol plug-in, and
- viii) providing the response data to a protocol manager.

20. The method of claim 19 further comprising displaying the response data to the user and storing the response data in a log file.

* * * * *

UNITED STATES PATENT AND TRADEMARK OFFICE
CERTIFICATE OF CORRECTION

PATENT NO. : 9,521,062 B2
APPLICATION NO. : 13/242546
DATED : December 13, 2016
INVENTOR(S) : Don R. Anderson, Jr. et al.

It is certified that error appears in the above-identified patent and that said Letters Patent is hereby corrected as shown below:

On the Title Page

Column 1, (73) Assignee, Line 2, delete "TN" and insert --IN--.

In the Drawings

Sheet 4 of 13, Reference Numeral 414 (Second Occurrence), Fig. 4, delete "414" and insert --416--.

In the Specification

Column 5, Detailed Description, Line 63, delete "414" and insert --416--.
Column 17, Detailed Description, Line 20, delete "1102" and insert --1110--.
Column 17, Detailed Description, Line 35, delete "1150" and insert --512--.
Column 17, Detailed Description, Line 37, delete "1150" and insert --512--.
Column 18, Detailed Description, Line 31, delete "1235" and insert --1234--.
Column 18, Detailed Description, Line 36, delete "1246" and insert --1248--.

In the Claims

Column 27, Claim 1, Line 55, delete "too" and insert --tool--.
Column 28, Claim 1, Line 55, after "definition", delete "the" and insert --file--.
Column 28, Claim 1, Line 57, after "definition", delete "the" and insert --file--.
Column 28, Claim 1, Line 59, after "definition", delete "the" and insert --file--.
Column 28, Claim 1, Line 64, after "definition", delete "the" and insert --file--.
Column 29, Claim 1, Line 40, delete "the" and insert --file--.

Signed and Sealed this
Fifteenth Day of August, 2017

Joseph Matal
Performing the Functions and Duties of the
Under Secretary of Commerce for Intellectual Property and
Director of the United States Patent and Trademark Office